(12) United States Patent
Pintor et al.

(10) Patent No.: US 8,579,926 B2
(45) Date of Patent: Nov. 12, 2013

(54) PLAQUE REMOVAL DEVICE WITH ROTATABLE CUTTING ELEMENT

(75) Inventors: Rafael Pintor, San Diego, CA (US); Bradley Steven Culbert, Rancho Santa Margarita, CA (US); Harold Alexander Heitzmann, Irvine, CA (US); Bruce D. Stambaugh, Anaheim, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/305,000

(22) Filed: Nov. 28, 2011

(65) Prior Publication Data

US 2012/0071907 A1     Mar. 22, 2012

Related U.S. Application Data

(63) Continuation of application No. 12/871,780, filed on Aug. 30, 2010, now abandoned, which is a continuation of application No. 11/490,620, filed on Jul. 21, 2006, now Pat. No. 7,842,055, which is a continuation of application No. 10/200,475, filed on Jul. 19, 2002, now Pat. No. 7,235,088, which is a continuation of application No. 09/656,635, filed on Sep. 7, 2000, now Pat. No. 6,482,217.

(51) Int. Cl.
    *A61B 17/22*     (2006.01)
(52) U.S. Cl.
    USPC ............................................... 606/159
(58) Field of Classification Search
    USPC .......... 606/159, 170, 180, 194; 600/564–568; 604/107, 171, 264, 22
    See application file for complete search history.

(56) References Cited

U.S. PATENT DOCUMENTS

| | | |
|---|---|---|
| 1,481,078 A | 1/1924 | Albertson |
| 2,701,559 A | 2/1955 | Cooper |
| 2,850,007 A | 9/1958 | Lingley |
| 3,064,651 A | 11/1962 | Henderson |
| 3,082,805 A | 3/1963 | Royce |
| 3,614,953 A | 10/1971 | Moss |
| 3,683,891 A | 8/1972 | Eskridge et al. |
| 3,732,858 A | 5/1973 | Banko |
| 3,749,085 A | 7/1973 | Willson et al. |
| 3,800,783 A | 4/1974 | Jamshidi |
| 3,845,375 A | 10/1974 | Stiebel |
| 3,937,222 A | 2/1976 | Banko |

(Continued)

FOREIGN PATENT DOCUMENTS

| | | |
|---|---|---|
| CA | 2000621 A1 | 4/1990 |
| DE | 8900059 U1 | 5/1989 |

(Continued)

OTHER PUBLICATIONS

Translation of Aug. 15, 2007 mailed Japanese Patent Office Action, Application No. 1999-139033 (4 pages).

(Continued)

*Primary Examiner* — Tuan V Nguyen
(74) *Attorney, Agent, or Firm* — Alana T. Bergman, Esq.

(57) ABSTRACT

An elongate tubular body with a rotatable cutting element is provided. An opening is provided near the distal end of the tubular body, and the cutting element may be partially exposed through the opening. The cutting element is configured to remove plaque from the wall of a body lumen. A distal segment may be coupled to the distal end of the tubular body and may have a distal port for slidably receiving a guidewire therethrough.

19 Claims, 22 Drawing Sheets

(56) References Cited

U.S. PATENT DOCUMENTS

| | | |
|---|---|---|
| 3,945,375 A | 3/1976 | Banko |
| 3,976,077 A | 8/1976 | Kerfoot, Jr. |
| 4,007,732 A | 2/1977 | Kvavle et al. |
| 4,020,847 A | 5/1977 | Clark, III |
| 4,030,503 A | 6/1977 | Clark, III |
| 4,038,985 A | 8/1977 | Chiulli |
| 4,112,708 A | 9/1978 | Fukuda |
| 4,177,797 A | 12/1979 | Baylis et al. |
| 4,273,128 A | 6/1981 | Lary |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,732,154 A | 3/1988 | Shiber |
| 4,745,919 A | 5/1988 | Bundey et al. |
| 4,747,406 A | 5/1988 | Nash |
| 4,747,821 A | 5/1988 | Kensey et al. |
| 4,754,755 A | 7/1988 | Husted |
| 4,765,332 A | 8/1988 | Fischell et al. |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,819,634 A | 4/1989 | Shiber |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMichael et al. |
| 4,883,458 A | 11/1989 | Shiber |
| 4,886,490 A | 12/1989 | Shiber |
| 4,887,613 A | 12/1989 | Farr et al. |
| 4,894,051 A | 1/1990 | Shiber |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,950,238 A | 8/1990 | Sullivan |
| 4,957,482 A | 9/1990 | Shiber |
| 4,966,604 A | 10/1990 | Reiss |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,026,384 A | 6/1991 | Farr et al. |
| 5,030,201 A | 7/1991 | Palestrant |
| 5,047,040 A | 9/1991 | Simpson et al. |
| 5,049,124 A | 9/1991 | Bales, Jr. |
| 5,064,435 A | 11/1991 | Porter |
| 5,071,425 A | 12/1991 | Gifford, III et al. |
| 5,074,841 A | 12/1991 | Ademovic et al. |
| 5,077,506 A | 12/1991 | Krause et al. |
| 5,078,722 A | 1/1992 | Stevens |
| 5,087,265 A | 2/1992 | Summers |
| 5,092,839 A | 3/1992 | Kipperman |
| 5,092,873 A | 3/1992 | Simpson et al. |
| 5,100,426 A | 3/1992 | Nixon |
| 5,112,345 A | 5/1992 | Farr |
| 5,114,399 A | 5/1992 | Kovalcheck |
| 5,135,531 A | 8/1992 | Shiber |
| 5,154,705 A | 10/1992 | Fleischhacker et al. |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,192,291 A | 3/1993 | Pannek, Jr. |
| 5,195,956 A | 3/1993 | Stockmeier |
| 5,222,966 A | 6/1993 | Perkins et al. |
| 5,224,945 A | 7/1993 | Pannek, Jr. |
| 5,242,460 A | 9/1993 | Klein et al. |
| 5,242,461 A | 9/1993 | Kortenbach et al. |
| 5,263,959 A | 11/1993 | Fischell |
| 5,267,955 A | 12/1993 | Hanson |
| 5,269,793 A | 12/1993 | Simpson |
| 5,273,526 A | 12/1993 | Dance et al. |
| 5,284,486 A | 2/1994 | Kotula et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,314,438 A | 5/1994 | Shturman |
| 5,322,508 A | 6/1994 | Viera |
| 5,324,300 A | 6/1994 | Elias et al. |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,366,463 A | 11/1994 | Ryan |
| 5,370,609 A | 12/1994 | Drasler et al. |
| 5,370,651 A | 12/1994 | Summers |
| 5,372,601 A | 12/1994 | Lary |
| 5,373,619 A | 12/1994 | Fleischhacker et al. |
| 5,378,234 A | 1/1995 | Hammerslag et al. |
| 5,395,311 A | 3/1995 | Andrews |
| 5,395,335 A | 3/1995 | Jang |
| 5,397,345 A | 3/1995 | Lazarus |
| 5,403,334 A | 4/1995 | Evans et al. |
| 5,409,454 A | 4/1995 | Fischell et al. |
| 5,423,740 A | 6/1995 | Sullivan |
| 5,423,799 A | 6/1995 | Shiu |
| 5,423,846 A | 6/1995 | Fischell |
| 5,431,673 A | 7/1995 | Summers et al. |
| 5,441,510 A | 8/1995 | Simpson et al. |
| 5,443,497 A | 8/1995 | Venbrux |
| 5,451,233 A | 9/1995 | Yock |
| 5,454,809 A | 10/1995 | Janssen |
| 5,489,295 A | 2/1996 | Piplani et al. |
| 5,496,267 A | 3/1996 | Drasler et al. |
| 5,501,694 A | 3/1996 | Ressemann et al. |
| 5,507,292 A | 4/1996 | Jang et al. |
| 5,507,760 A | 4/1996 | Wynne et al. |
| 5,507,761 A | 4/1996 | Duer |
| 5,512,044 A | 4/1996 | Duer |
| 5,514,115 A | 5/1996 | Frantzen et al. |
| 5,522,825 A | 6/1996 | Kropf et al. |
| 5,522,880 A | 6/1996 | Barone et al. |
| 5,531,690 A | 7/1996 | Solar |
| 5,554,163 A | 9/1996 | Shturman |
| 5,556,408 A | 9/1996 | Farhat |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |

(56) References Cited

U.S. PATENT DOCUMENTS

| | | | |
|---|---|---|---|
| 5,569,277 A | 10/1996 | Evans et al. |
| 5,569,279 A | 10/1996 | Rainin |
| 5,571,130 A | 11/1996 | Simpson et al. |
| 5,575,817 A | 11/1996 | Martin |
| 5,584,843 A | 12/1996 | Wulfman et al. |
| 5,609,605 A | 3/1997 | Marshall et al. |
| 5,618,293 A | 4/1997 | Sample et al. |
| 5,624,457 A | 4/1997 | Farley et al. |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,643,296 A | 7/1997 | Hunderlmark et al. |
| 5,649,941 A | 7/1997 | Lary |
| 5,662,671 A | 9/1997 | Barbut et al. |
| 5,665,098 A | 9/1997 | Kelly et al. |
| 5,669,920 A | 9/1997 | Conley et al. |
| 5,676,696 A | 10/1997 | Marcade |
| 5,676,697 A | 10/1997 | McDonald |
| 5,681,336 A | 10/1997 | Clement et al. |
| 5,683,449 A | 11/1997 | Marcade |
| 5,683,453 A | 11/1997 | Palmaz |
| 5,695,506 A | 12/1997 | Pike et al. |
| 5,695,507 A | 12/1997 | Auth et al. |
| 5,697,944 A | 12/1997 | Lary |
| 5,700,240 A | 12/1997 | Barwick, Jr. et al. |
| 5,707,350 A | 1/1998 | Krause et al. |
| 5,707,383 A | 1/1998 | Bays et al. |
| 5,713,913 A | 2/1998 | Lary et al. |
| 5,728,123 A | 3/1998 | Lemelson et al. |
| 5,733,296 A | 3/1998 | Rogers et al. |
| 5,735,816 A | 4/1998 | Lieber et al. |
| 5,766,192 A | 6/1998 | Zacca |
| 5,772,674 A | 6/1998 | Nakhjavan |
| 5,776,153 A | 7/1998 | Rees |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,807,329 A | 9/1998 | Gelman |
| 5,820,592 A | 10/1998 | Hammerslag |
| 5,824,039 A | 10/1998 | Piplani et al. |
| 5,824,055 A | 10/1998 | Spiridigliozzi et al. |
| 5,827,229 A | 10/1998 | Auth et al. |
| 5,827,304 A | 10/1998 | Hart |
| 5,827,322 A | 10/1998 | Williams |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,871,536 A | 2/1999 | Lazarus |
| 5,873,882 A | 2/1999 | Straub et al. |
| 5,876,414 A | 3/1999 | Straub |
| 5,938,645 A | 8/1999 | Gordon |
| 5,938,672 A | 8/1999 | Nash |
| 5,941,869 A | 8/1999 | Patterson et al. |
| 6,001,112 A | 12/1999 | Taylor |
| 6,027,514 A | 2/2000 | Stine et al. |
| 6,032,673 A | 3/2000 | Savage et al. |
| 6,095,990 A | 8/2000 | Parodi |
| 6,152,909 A | 11/2000 | Bagaoisan et al. |
| 6,156,046 A | 12/2000 | Passafaro et al. |
| 6,159,195 A | 12/2000 | Ha et al. |
| 6,206,898 B1 | 3/2001 | Honeycutt et al. |
| 6,238,405 B1 | 5/2001 | Findlay, III et al. |
| 6,299,622 B1 | 10/2001 | Snow et al. |
| 6,312,444 B1 | 11/2001 | Barbut |
| 6,447,525 B2 | 9/2002 | Follmer et al. |
| 6,451,036 B1 | 9/2002 | Heitzmann et al. |
| 6,454,779 B1 | 9/2002 | Taylor |
| 6,482,217 B1 | 11/2002 | Pintor et al. |
| 6,565,588 B1 | 5/2003 | Clement et al. |
| 6,623,437 B2 | 9/2003 | Hinchliffe et al. |
| 6,623,495 B2 | 9/2003 | Findlay, III et al. |
| 6,638,233 B2 | 10/2003 | Corvi et al. |
| 6,652,505 B1 | 11/2003 | Tsugita |
| 6,656,195 B2 | 12/2003 | Peters et al. |
| 6,666,874 B2 | 12/2003 | Heitzmann et al. |
| 6,790,204 B2 | 9/2004 | Zadno-Azizi et al. |
| 6,790,215 B2 | 9/2004 | Findlay et al. |
| 6,818,001 B2 | 11/2004 | Wulfman et al. |
| 6,843,797 B2 | 1/2005 | Nash et al. |
| 6,849,068 B1 | 2/2005 | Bagaoisan et al. |
| 7,172,610 B2 | 2/2007 | Heitzmann et al. |
| 7,235,088 B2 | 6/2007 | Pintor et al. |
| 7,479,147 B2 | 1/2009 | Honeycutt |
| 7,771,445 B2 | 8/2010 | Heitzmann et al. |
| 7,842,055 B2 | 11/2010 | Pintor et al. |
| 2001/0004700 A1 | 6/2001 | Honeycutt et al. |
| 2001/0044622 A1 | 11/2001 | Vardi et al. |
| 2002/0058904 A1 | 5/2002 | Boock |
| 2002/0077642 A1 | 6/2002 | Patel et al. |
| 2002/0095141 A1 | 7/2002 | Belef |
| 2002/0177800 A1 | 11/2002 | Bagaoisan |
| 2003/0023263 A1 | 1/2003 | Krolik |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0087988 A1 | 5/2004 | Heitzmann et al. |
| 2005/0004594 A1 | 1/2005 | Nool |
| 2006/0235334 A1 | 10/2006 | Corvi et al. |
| 2006/0259052 A1 | 11/2006 | Pintor et al. |
| 2007/0225739 A1 | 9/2007 | Pintor et al. |
| 2010/0174302 A1 | 7/2010 | Heitzmann et al. |

FOREIGN PATENT DOCUMENTS

| | | |
|---|---|---|
| DE | 37 32 236 C1 | 12/1998 |
| DE | 297 22 136 U1 | 4/1999 |
| EP | 0 086 048 A2 | 8/1983 |
| EP | 0 291 170 A1 | 11/1988 |
| EP | 0 330 843 A1 | 9/1989 |
| EP | 0 373 927 A2 | 6/1990 |
| EP | 0 421 457 A1 | 4/1991 |
| EP | 0 448 859 A2 | 10/1991 |
| EP | 0 463 798 A1 | 1/1992 |
| EP | 0 514 810 A1 | 11/1992 |
| EP | 0 533 320 A2 | 3/1993 |
| EP | 0 657 140 A1 | 6/1995 |
| GB | 2 093 353 A | 9/1982 |
| GB | 2 210 965 A | 6/1989 |
| JP | 2-271847 A | 11/1990 |
| JP | 3-186256 A | 8/1991 |
| JP | 4-200459 A | 7/1992 |
| JP | 5-42162 A | 2/1993 |
| JP | 5-56984 A | 3/1993 |
| JP | 5-184679 A | 7/1993 |
| JP | 6-205785 A | 7/1994 |
| JP | 6-269460 A | 9/1994 |
| JP | 6-511417 A | 12/1994 |
| JP | 7-075611 B | 8/1995 |
| JP | 11-347040 A | 12/1999 |
| SU | 442795 A1 | 9/1974 |
| SU | 665908 A1 | 6/1979 |
| WO | WO 89/06517 A1 | 7/1989 |
| WO | WO 93/13716 A1 | 7/1993 |
| WO | WO 93/13717 A1 | 7/1993 |
| WO | WO 94/11053 A1 | 5/1994 |
| WO | WO 95/21576 A1 | 8/1995 |
| WO | WO 96/11648 A1 | 4/1996 |
| WO | WO 97/46164 A1 | 12/1997 |
| WO | WO 98/04199 A1 | 2/1998 |
| WO | WO 98/24372 A1 | 6/1998 |
| WO | WO 98/24373 A1 | 6/1998 |
| WO | WO 99/52454 A1 | 10/1999 |
| WO | WO 01/30433 A1 | 5/2001 |
| WO | WO 01/43809 A1 | 6/2001 |

OTHER PUBLICATIONS

Japanese Office Action, and its English translation, issued Nov. 10, 2011 in Japanese Patent Application No. 2002-524416 (5 pages).

(56) References Cited

OTHER PUBLICATIONS

German Office Action, and its English translation, issued Jun. 23, 2010 in German Patent Application No. 100 09 512.7 (10 pages).
Abstract for JP 6-205785 A (2 pages).
Abstract for JP 11-347040 A (1 page).
Japanese Office Action, and its English translation, issued Mar. 1, 2011 in Japanese Patent Application No. 2002-524416 (6 pages).
Abstract for EP 0 330 843 A1 (1 page).
Abstract for EP 0 421 457 A1 (1 page).
Abstract for JP 2-271847 A (2 pages).
Abstract for JP 3-186256 A (2 pages).
Abstract for JP 4-200459 A (2 pages).
Abstract for JP 5-184679 A (2 pages).
Abstract for JP 5-42162 A (2 pages).
Abstract for JP 5-56984 (2 pages).
Abstract for JP 6-269460 A (2 pages).
Abstract for WO 89/06517 A1 (1 page).
European Patent Office Examination Report dated Jul. 28, 2006, Application No. 00905773.8, Applicant: Endicor Medical, Inc. (5 pages).
European Patent Office Examination Report dated Aug. 4, 2006, Application No. 99919808.8, Applicant: Endicor Medical, Inc. (5 pages).
European Patent Office Examination Report dated Aug. 30, 2006, Application No. 01973700.6, Applicant: Endicor Medical, Inc. (4 pages).
European Search Report dated Jan. 16, 2008 in Application No. 07020538.0 (7 pages).

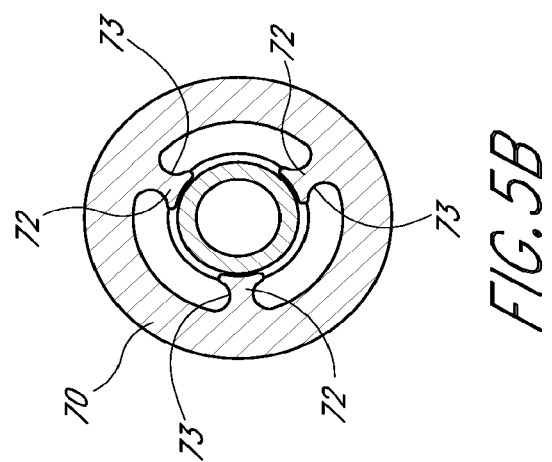
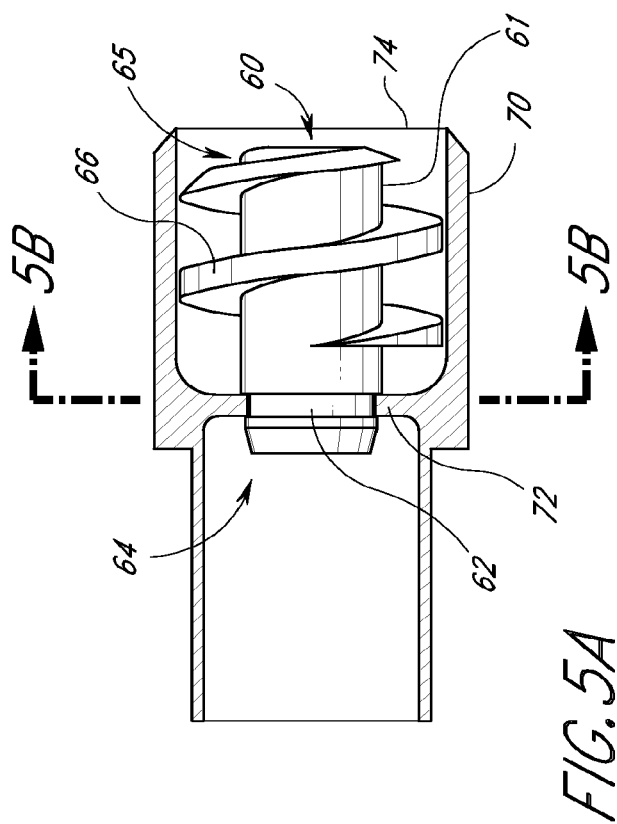

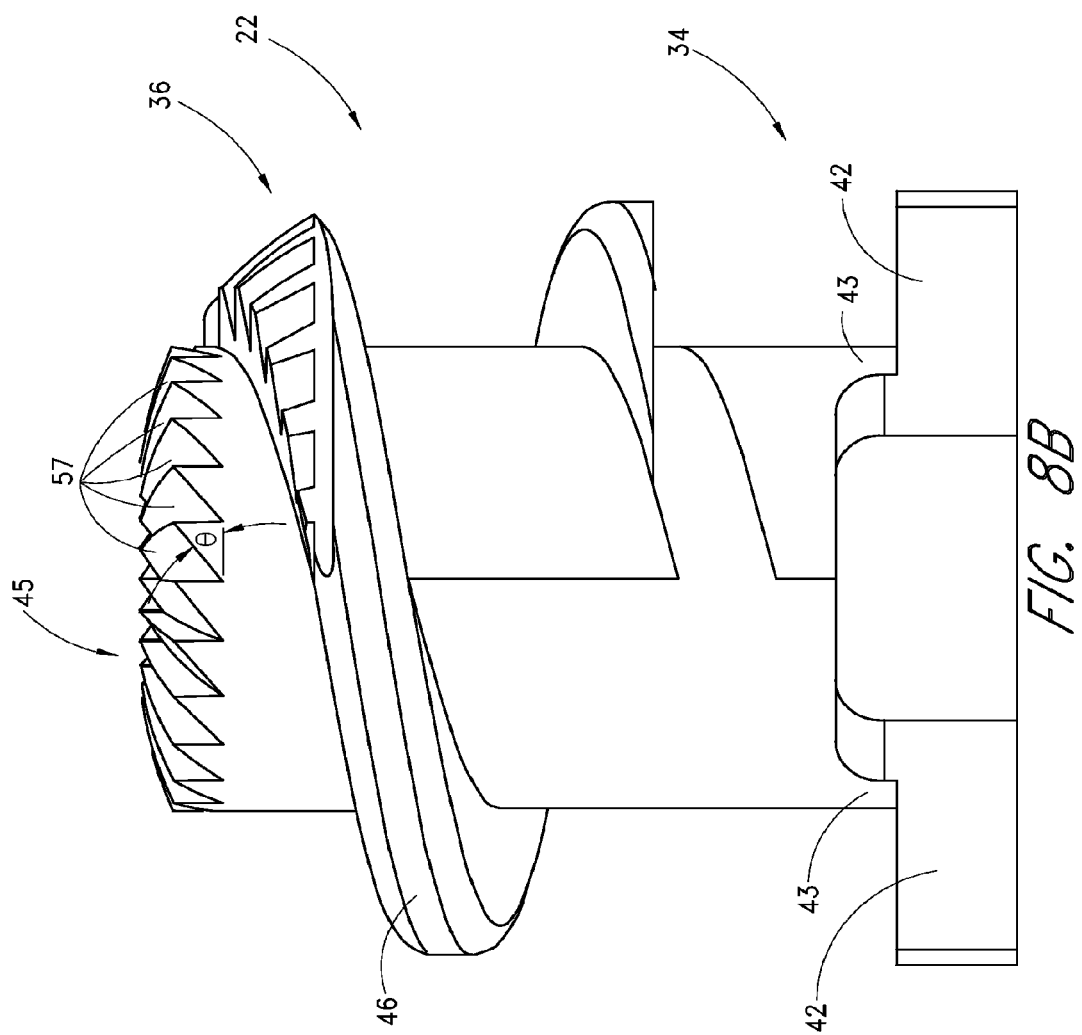

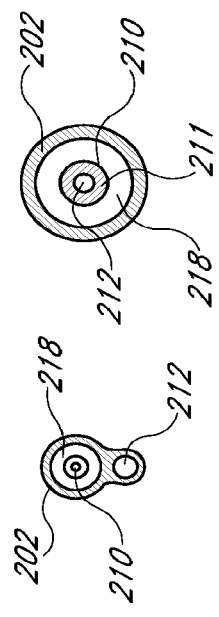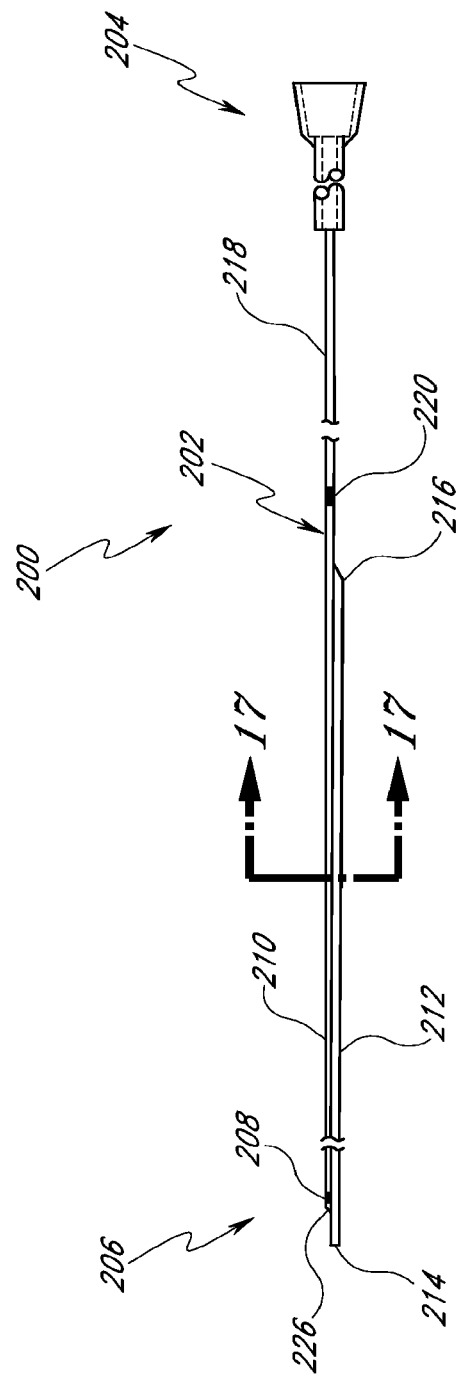
FIG. 17A  FIG. 17B
FIG. 16

PLAQUE REMOVAL DEVICE WITH ROTATABLE CUTTING ELEMENT

CROSS-REFERENCES TO RELATED APPLICATIONS

This application is a continuation of U.S. patent application Ser. No. 12/871,780, filed Aug. 30, 2010, now abandoned, which is a continuation of U.S. patent application Ser. No. 11/490,620, filed Jul. 21, 2006, now U.S. Pat. No. 7,842,055, which is a continuation of U.S. patent application Ser. No. 10/200,475, filed Jul. 19, 2002, now U.S. Pat. No. 7,235,088, which is a continuation of U.S. patent application Ser. No. 09/656,635, filed Sep. 7, 2000, now U.S. Pat. No. 6,482,217. The disclosures of the above-referenced applications are hereby expressly incorporated by reference in their entirety. Also incorporated by reference in their entirety are U.S. patent application Ser. No. 09/398,241, filed Sep. 17, 1999, now U.S. Pat. No. 6,666,874, which is a continuation-in-part of U.S. patent application Ser. No. 09/260,199, filed on Mar. 1, 1999, now U.S. Pat. No. 6,206,898, which is a continuation-in-part of U.S. patent application Ser. No. 09/058,513, filed on Apr. 10, 1998, now U.S. Pat. No. 6,001,112.

BACKGROUND OF THE INVENTION

The present invention generally relates to thrombectomy or atherectomy devices and, more particularly, to thrombectomy catheter devices adapted to access vasculature above the carotid arteries.

A variety of techniques and instruments have been developed to remove obstructive material in arteries or other body passageways or to repair the arteries or body passageways. A frequent objective of such techniques and instruments is the removal of atherosclerotic plaques in a patient's arteries. The buildup of fatty deposits (atheromas) in the intimal layer (under the endothelium of a patient's blood vessels) characterizes atherosclerosis. Over time, what is initially deposited as relatively soft, cholesterol-rich atheromatous material often hardens into a calcified atherosclerotic plaque. The atheromas may be referred to as stenotic lesions or stenoses while the blocking material may be referred to as stenotic material. If left untreated, such stenoses can so sufficiently reduce perfusion that angina, hypertension, myocardial infarction, strokes and the like may result.

Several kinds of atherectomy devices have been developed for attempting to remove some or all of such stenotic material. In one type of device, such as that shown in U.S. Pat. No. 5,092,873 (Simpson), a cylindrical housing, carried at the distal end of a catheter, has a portion of its side-wall cut out to form a window into which the atherosclerotic plaque can protrude when the device is positioned next to the plaque. An atherectomy blade, disposed within the housing, is then advanced the length of the housing to lance the portion of the atherosclerotic plaque that extends into the housing cavity. While such devices provide for directional control in selection of tissue to be excised, the length of the portion excised at each pass of the atherectomy blade is necessarily limited to the length of the cavity in the device. The length and relative rigidity of the housing limits the maneuverability and therefore also limits the utility of the device in narrow and tortuous arteries such as coronary arteries. Such devices are also generally limited to lateral cutting relative to the longitudinal axis of the device.

Another approach, which solves some of the problems relating to removal of atherosclerotic plaque in narrow and tortuous passageways, involves the use of an abrading device carried at the distal end of a flexible drive shaft. Examples of such devices are illustrated in U.S. Pat. No. 4,990,134 (Auth) and U.S. Pat. No. 5,314,438 (Shturman). In the Auth device, abrasive material such as diamond grit (diamond particles or dust) is deposited on a rotating burr carried at the distal end of a flexible drive shaft. In the Shturman device, a thin layer of abrasive particles is bonded directly to the wire turns of an enlarged diameter segment of the drive shaft. The abrading device in such systems is rotated at speeds up to 200,000 rpm or more, which, depending on the diameter of the abrading device utilized, can provide surface speeds of the abrasive particles in the range of 40 ft/sec. According to Auth, at surface speeds below 40 ft/sec his abrasive burr will remove hardened atherosclerotic materials but will not damage normal elastic soft tissue of the vessel wall. See, e.g., U.S. Pat. No. 4,990,134 at col. 3, lines 20-23.

However, not all atherosclerotic plaques, and certainly not all thrombi, are hardened and calcified. Moreover, the mechanical properties of soft plaques and thrombi are very often quite close to the mechanical properties of the soft tissue of the vessel wall. Thus, one cannot always rely entirely on the differential cutting properties of such abrasives to remove atherosclerotic material from an arterial wall, particularly where one is attempting to remove all or almost all of the atherosclerotic material.

Moreover, a majority of atherosclerotic lesions are asymmetrical (i.e., the atherosclerotic plaque is thicker on one side of the artery than on the other). As will be understood, the stenotic material will be entirely removed on the thinner side of an eccentric lesion before it will be removed on the thicker side of the lesion. Accordingly, during removal of the remaining thicker portion of the atherosclerotic plaque, the abrasive burr of the Auth device or the abrasive-coated enlarged diameter segment of the drive shaft of the Shturman device will necessarily engage healthy tissue on the side that has been cleared. Indeed, lateral pressure by such healthy tissue against the abrading device is inherently required to keep the abrading device in contact with the remaining stenotic tissue on the opposite wall of the passageway. For stenotic lesions that are entirely on one side of an artery (a relatively frequent condition), the healthy tissue across from the stenotic lesion will be exposed to and in contact with the abrading device for substantially the entire procedure. Moreover, pressure from that healthy tissue against the abrading device will be, in fact, the only pressure urging the abrading device against the atherosclerotic plaque. Under these conditions, a certain amount of damage to the healthy tissue is almost unavoidable, even though undesirable, and there is a clear risk of perforation or proliferative healing response. In some cases, the "healthy tissue" across from a stenotic lesion may be somewhat hardened by the interaction (i.e., it has diminished elasticity); under such circumstances, the differential cutting phenomenon described by Auth will also be diminished, resulting in a risk that this "healthy" tissue may also be removed, potentially causing perforation.

Additional, unique challenges are encountered in the design of a rotational atherectomy or thrombectomy catheter which is intended to access the remote coronary arteries or the intracranial vasculature. For example, the prior art catheters generally are either too large in diameter to access remote vasculature, or insufficiently flexible, particularly at the distal, cutting tip, to navigate tortuous vasculature.

Thus, notwithstanding the foregoing and other efforts to design a rotational atherectomy or thrombectomy device, there remains a need for a device that can advance through soft thrombus while providing minimal risk of thrombus dislodgement and consequent embolization, and risk of injury to the surrounding vessel wall. In addition, the device preferably exhibits sufficient flexibility and other characteristics to enable access to the arterial vasculature distal to the internal carotid and basilar arteries.

SUMMARY OF THE INVENTION

There is provided in accordance with one aspect of the present invention a neurothrombectomy catheter adapted to access remote intracranial vasculature. The thrombectomy catheter comprises an elongate flexible tubular body having a sufficiently small outside diameter and sufficient kink resistance and pushability to navigate through the common carotid artery, the internal carotid artery, and at least as far distal as the M2, or sylvian, segment of the middle cerebral artery. Rotation of a cutter tip in a distal portion of the catheter, and application of vacuum through the catheter, enables removal of thrombus from the vicinity of the bifurcation in the distal M1 segment of the middle cerebral artery, or other remote location elsewhere in the intracranial, coronary, or other vasculature of a patient.

In accordance with another aspect of the present invention, there is provided a rotational neurothrombectomy catheter. The catheter comprises an elongate flexible tubular body, having a proximal end and a distal end, and a distal segment with an outside diameter small enough to access the M1, or horizontal, segment of the middle cerebral artery and sufficiently kink-resistant to enable rotation of a rotatable tip therein. A rotatable element extends through the body, and is connected at its distal end to a rotatable tip in the distal end of the body. A control is provided on the proximal end of the body. At least one radially inwardly extending stationary cutting member is provided on the tubular body, and at least one radially outwardly extending flange on the rotatable tip is provided for cooperating with the stationary cutting member to cut material drawn into the tubular body.

In one embodiment, two radially outwardly extending flanges on the rotatable tip cooperate with two stationary cutting members on the tubular body.

In accordance with a further aspect of the present invention, there is provided a method of removing material from the middle cerebral artery. The method comprises the steps of providing an elongate flexible tubular body, having a proximal end and a distal end, a rotatable tip at the distal end of the tubular body, and at least one stationary cutting member on the tubular body which cooperates with at least one flange on the rotatable tip. The distal end of the tubular body is advanced transluminally through the internal carotid artery at least as distal as the M1 segment of the middle cerebral artery. The tip is rotated, and portions of material from the middle cerebral artery are drawn proximally past the rotated tip so that the material is cut by the action of the flange rotating past the stationary member.

In one embodiment, the drawing step is accomplished by applying vacuum to the proximal end of the tubular body.

Further features and advantages of the present invention will become apparent to those of skill in the art in view of the disclosure herein, when considered together with the attached drawings and claims.

BRIEF DESCRIPTION OF THE DRAWINGS

FIG. 5A is a partially sectioned side view of another embodiment of the cutter and housing.

FIG. 5B is a cross-sectional view of the cutter and housing of FIG. 5A taken along the lines 5B-5B.

FIG. 8B is a side view of the serrated cutter of FIG. 8A.

FIG. 16 is a side elevational cross-section of a neurothrombectomy catheter in accordance with one aspect of the present invention.

FIG. 17A is a cross-sectional view taken along the line 17-17 of FIG. 16, illustrating a monorail configuration.

FIG. 17B is an alternate cross-section taken along the line 17-17 in FIG. 16, illustrating an over the wire configuration.

DETAILED DESCRIPTION OF THE PREFERRED EMBODIMENT

Figure 1:
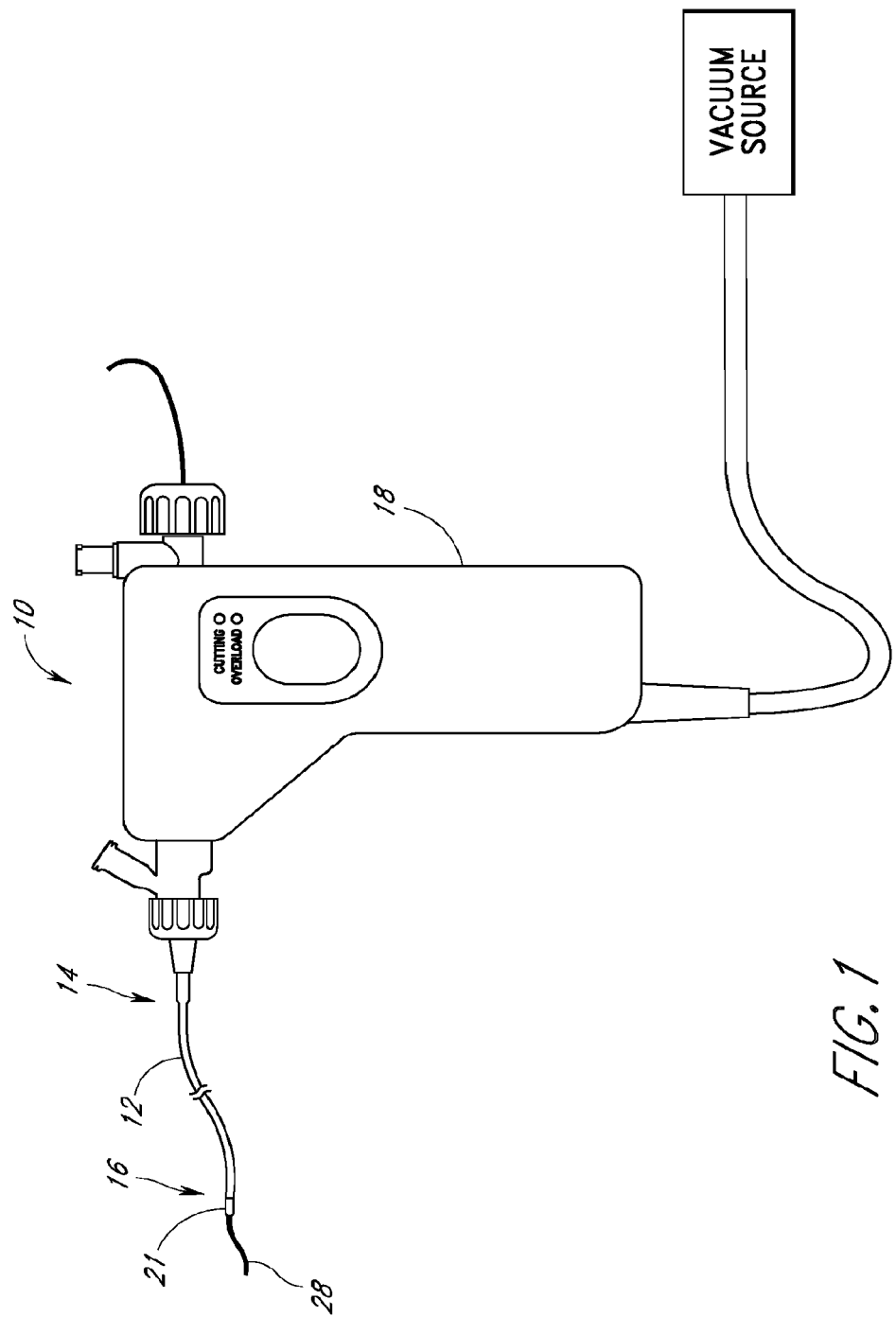
FIG. 1 is a schematic view of a device embodying the present invention.

With reference initially to FIG. 1, a surgical instrument, indicated generally by reference numeral 10 having features, aspects and advantages in accordance with the present invention is depicted therein. In general, the illustrative surgical instrument comprises an elongate flexible tubular body 12 having a proximal end 14 and a distal end 16. A control 18 is preferably provided at or near the proximal end 14 of the tubular body 12 for permitting manipulation of the instrument 10. The control 18 advantageously carries electronic controls and indicators as well as vacuum controls as will be discussed below.

Figure 2:
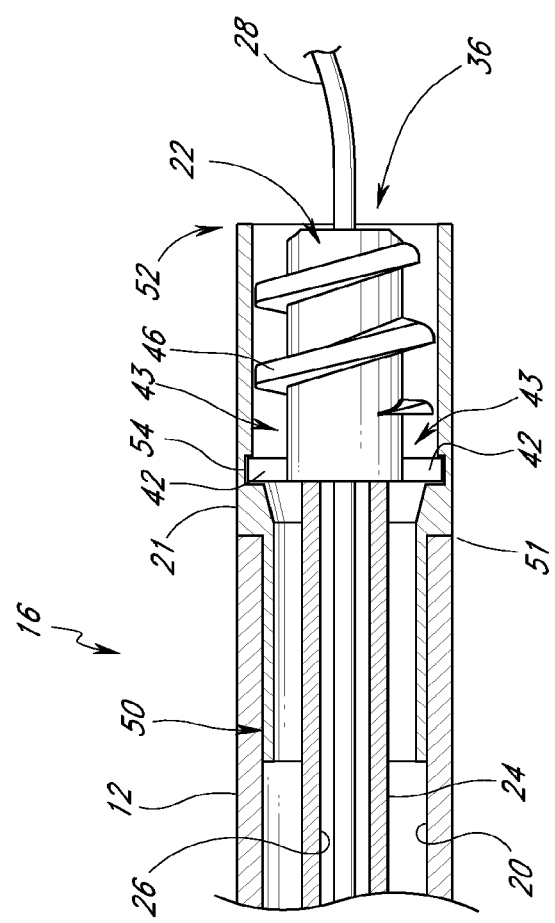
FIG. 2 is a partially sectioned side view of a distal end of the device of FIG. 1, showing an embodiment of the cutter assembly.

With reference now to the partially sectioned view of FIG. 2, the tubular body 12 preferably has an elongate central lumen 20. Desirably, the tubular body 12 has a cutter housing 21 for receiving a cutter 22 that may rotate therein. The illustrated cutter 22 is coupled to the control 18 for rotation by way of an elongate flexible drive shaft 24, as will be described below. In an over-the-wire embodiment, the drive shaft 24 is provided with an axially extending central lumen 26 for slidably receiving a guidewire 28 as will be understood by those of skill in the art. Moreover, in such configurations, the cutter 22 may also have a central lumen.

The diameter of the guidewire 28 is preferably in the range of about 0.010 inch to about 0.020 inch. The lengths of the guidewire 28 and the tubular body 12 may be varied to correspond to a distance between a percutaneous access site and a lesion being treated. For example, the guidewire 28 and the tubular body 12 should be long enough to allow the cutter 22 of the present surgical instrument 10 to track along the guidewire 28 and reach a target occlusion while also allowing a proximal portion of the guidewire 28 to remain exterior to the patient for manipulation by the clinician (not shown). In an application for removing coronary artery atheroma by way of a femoral artery access, guidewires having lengths from about 120 cm to about 160 cm may be used, and the length of the tubular body 12 may range between about 50 cm and about 150 cm, as will be understood by those of skill in art. For other applications, such as peripheral vascular procedures including recanalization of implanted vascular grafts, the length of the guidewire 28 and the tubular body 12 may depend upon the location of the graft or other treatment site relative to the percutaneous or surgical access site. Suitable guidewires for coronary artery applications include those manufactured by Guidant or Cordis.

Figure 4:
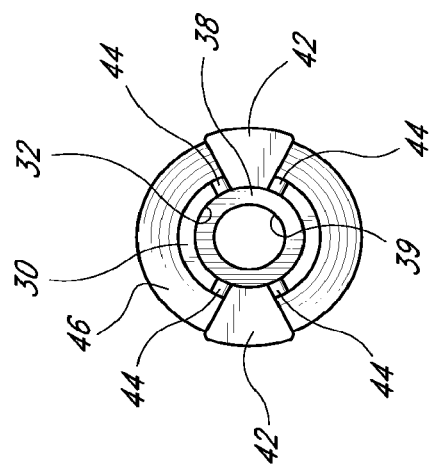
FIG. 4 is an end view of the cutter of FIG. 3 taken along the line 4-4.
Figure 3:
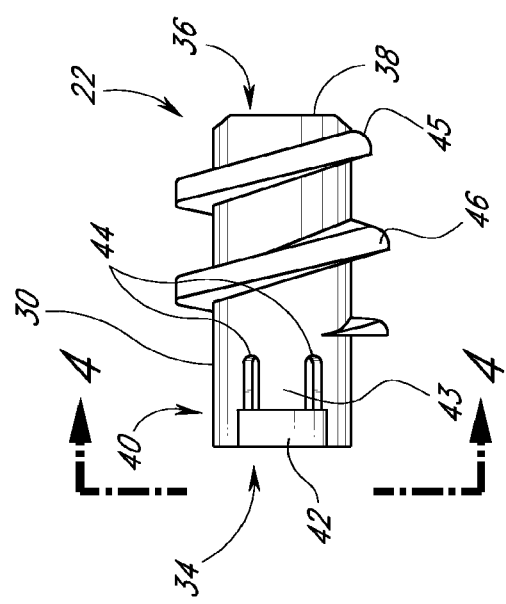
FIG. 3 is a side view of the cutter of FIG. 2.

With reference now to FIGS. 3 and 4, the illustrated cutter 22 includes a generally cylindrical sleeve shaped body 30 having a central lumen 32 (FIG. 4). The cylindrical body 30 of the cutter 22 generally has an external diameter of between about 0.035 inch and 0.092 inch. In one embodiment, the external diameter is approximately 0.042 inch. The body 30 has a wall thickness between about 0.003 inch and about 0.010 inch. In one embodiment, the wall thickness is about 0.009 inch. The length of one embodiment of the present cutter 22 from proximal end 34 to distal end 36 is approximately 0.096 inch but the length may vary from about 0.040 inch to about 0.120 inch or more, depending upon the intended use. In general, tip lengths of no more than about 0.100 inch are preferred; shorter tip lengths permit greater lateral flexibility and enable increased remote access as will be apparent to those of skill in the art.

With continued reference to FIG. 3, an end cap 38 may be formed on the distal end 36 of the present cutter tip 22. Specifically, the cylindrical body 30 may be machined to create an integral (i.e., one piece) end cap 38. The end cap 38 may have a thickness of approximately 0.007 inch; however, the end cap thickness may range from about 0.003 inch to about 0.020 inch. Additionally, it is contemplated that a discrete end cap 38 may also be separately machined and attached. For instance, the end cap 38 may be formed from a more lubricious material to reduce frictional contact between the guidewire 28 and the end cap 38. Such an end cap may be attached in any suitable manner. The end cap 38 preferably has an outside diameter that substantially corresponds to the outside diameter of the distal end 26 of the present cutter tip 22. The end cap outside diameter may, however, substantially correspond to the inside diameter of the cylindrical body in some embodiments.

The end cap 38 may also have a centrally located aperture 39. The aperture 39, if present, preferably has a diameter of between about 0.013 inch and about 0.025 inch. In one embodiment, the aperture 39 has a diameter of approximately 0.022 inch. Desirably, the aperture 39 may accommodate a guidewire 28 or allow fluids to flow therethrough. As will be appreciated, the cutter 22 may have a machined or otherwise integrally formed radially inwardly extending annular flange 41 (see FIG. 6). It is also anticipated that aspects of the present invention may also be practiced without employing an end cap or inwardly extending annular flange 41. In such configurations, the flange 41 may extend fully around the circumference of the cutter 22 or may have portions removed such that the annular flange 41 is actually a series of inwardly projecting tabs. Additionally, an outside distal edge of the end cap 38 or annular flange 41 is desirably broken, chamfered or rounded such that any sharp edge resulting from manufacturing may be removed, and such that the end cap may be rendered substantially atraumatic.

With reference now to FIGS. 2-4, a connector portion 40 is preferably provided at or near the proximal end 34 of the illustrated cutter 22 for securing the cutter 22 within the cutter housing 21 such that the cutter may rotate therein. Additionally, the connector portion 40 may be a mechanical, self-locking method to secure the rotating cutter 22 within the cutter housing 21 and to guard against undesired axial movement of the cutter 22 relative to the housing 21. In certain embodiments, axial movement of the cutter may be accommodated within the housing 21, and even within the tubular body 12, as will be discussed below in more detail.

As will be recognized by those of skill in the art, safety straps, redundant glue joints, crimping, and swaging are commonly used to create redundant failure protection for catheter cutter tips. The advantageous structure of the present connector portion 40 retains the cutter tip 22 within the cutter housing 21 and may reduce the need for such multiple redundancies. As will be described, the connector portion 40 may take various forms.

In embodiments similar to the one illustrated in FIGS. 2-4, the connector portion 40 generally comprises two outwardly extending radial supports, such as a set of wedge-shaped flanges 42. The flanges 42 may be formed by removing material from an annular circumferential flange at the proximal end 34 of the cutter 22. The flanges 42 may be formed into the illustrated wedge-shape, although other shapes may also be desirable. The flanges 42 may also be bent from a proximal extension of the wall of tubular body 30, or adhered or otherwise secured to the proximal end 34 of the cutter 22. Moreover, as will be recognized by one of ordinary skill in the art, the cutter 22 and flanges 42 may be cast or molded using any suitable method dependent upon the material chosen. As will be recognized by those of ordinary skill in the art, the flanges 42 may alternatively be connected to tubular body 30 at a point in between the proximal end 34 and the distal end 36 of the cutter tip.

Although two opposing flanges 42 are illustrated in FIGS. 2-4, three or more flanges 42 may be utilized, as will be apparent to those of skill in the art. In general, the flanges 42 should be evenly distributed around the circumference of the cutter 22 to improve balance during rotation of the cutter 22. For example, three flanges 42 would preferably extend radially outward from the cylindrical wall of the body 30 on approximately 120° centers. Similarly, four outwardly extending radial flanges 42 would preferably be located on approximately 90° centers.

Figure 8A:
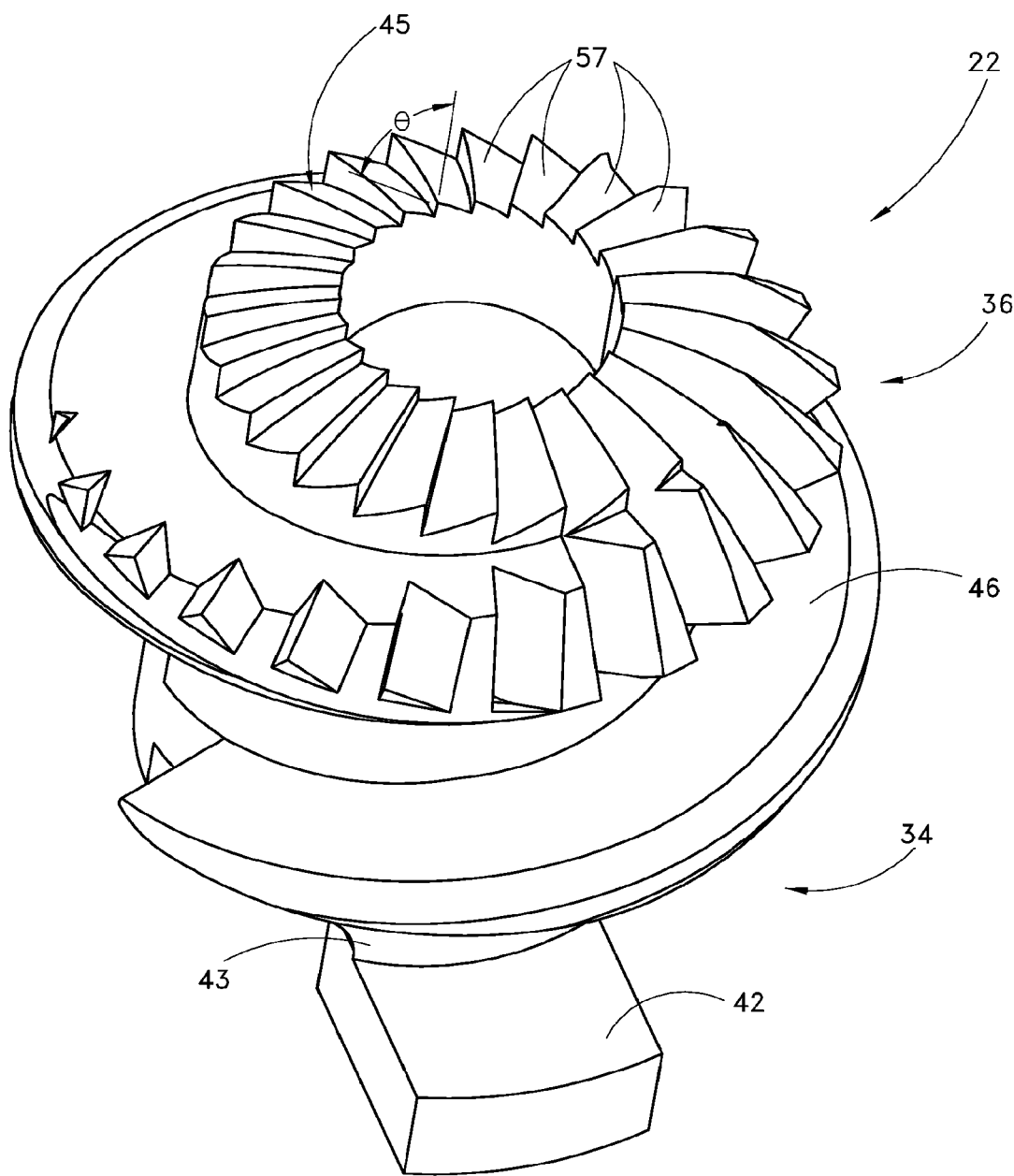
FIG. 8A is a top perspective view of a serrated cutter configured in accordance with certain features, aspects and advantages of the present invention.
Figure 8C:
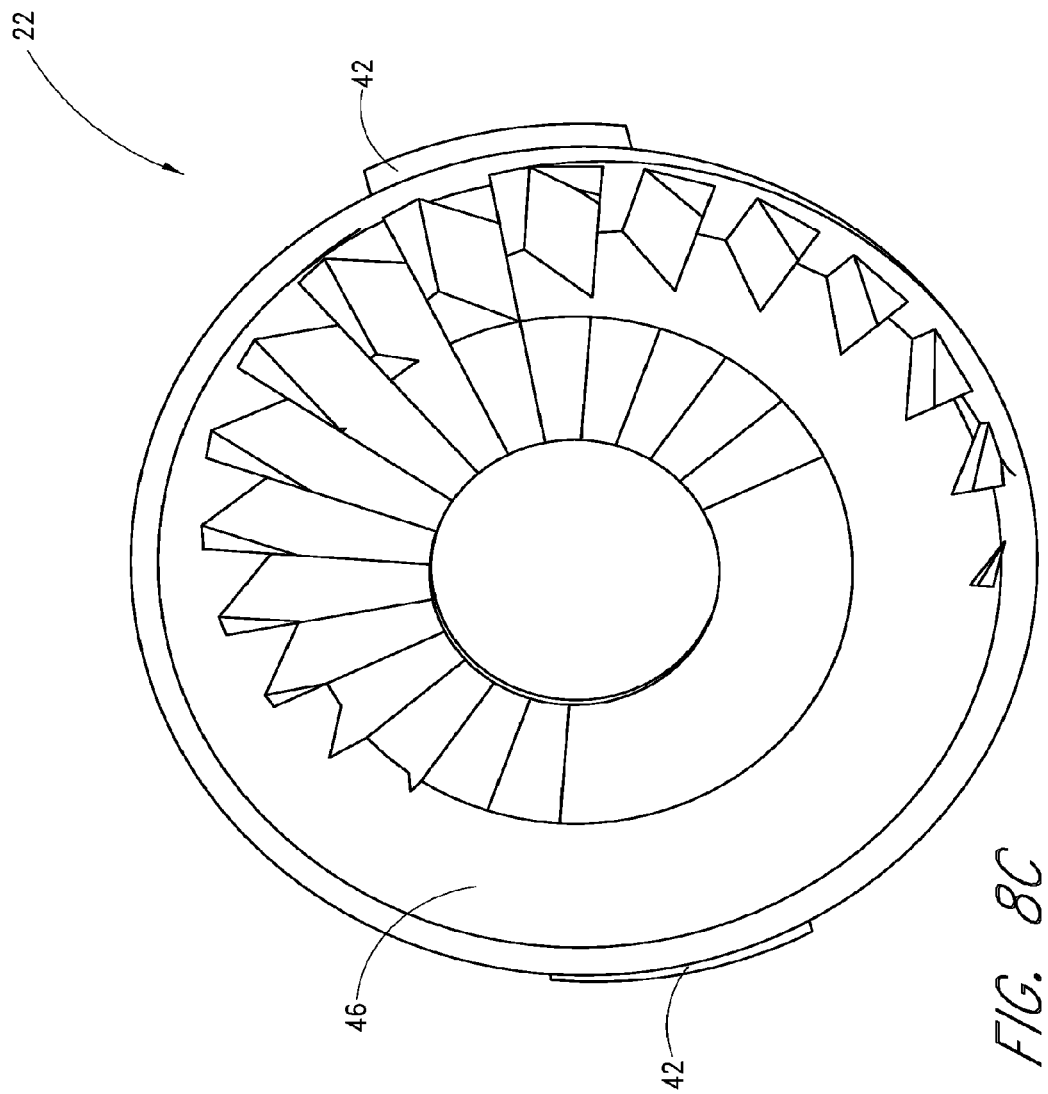
FIG. 8C is a top view of the serrated cutter of FIG. 8A.

With reference now to FIGS. 8A-8C, another configuration of the connector portion 40 is illustrated therein. In the illustrated configuration, the outwardly extending radial supports 42 are also formed by removing material from an annular circumferential flange at the proximal end of the cutter 22. The supports 42 are attached to the balance of the cutter 22 with tangs 43 that are carved from the cutter 22 when the supports 42 are formed. In this manner, the tangs 43 do not require the slots that form the arms described above. Of course, a combination of the slots and arms and the tangs without slots may also be used to attach the flange 42 to the cutter 22. In the illustrated embodiment, the tangs 43 preferably are between about 0.010 inch and about 0.050 inch in length. More preferably, the tangs 43 are about 0.015 inch long. In one embodiment, the tangs are about 0.25 inch long. The tangs also have a width between about 0.010 inch and about 0.050 inch. In a presently preferred embodiment, the tangs have a width of about 0.020 inch.

The illustrated connector portion 40 has an outside diameter taken about the opposing flanges 42 of approximately 0.071 inch. Generally, the outside diameter may range from about 0.057 inch to about 0.096 inch in a device intended for coronary artery applications. The thickness of the flanges 42 in the axial direction (i.e., the dimension normal to the increase in diameter resulting from the flanges) is about 0.010 inch but may range from about 0.004 inch to about 0.025 inch. In general, an outside diameter defined about the flanges 42 may be selected to cooperate with the inside diameter of an annular retaining race or groove 54 in the housing 21, discussed below, to axially retain the cutter 22 while permitting rotation of the cutter 22 relative to the housing 21. The thickness of the flanges 42 and the axial width of the retaining groove 54 also are generally designed to either allow axial movement of the cutter 22 within the housing 21 or to limit or eliminate substantial axial movement of the cutter 22 within the housing 21, as is discussed below.

With continued reference to now FIG. 3, each illustrated flange 42 is preferably attached to the cutter 22 by a spring arm 43. Each arm 43 is defined by two longitudinally extending slots 44 which are formed in the cylindrical wall of the body 30 adjacent each flange 42. The slots 44 are preferably about 0.005 inch in width; however the width may range from approximately 0.001 inch to approximately 0.025 inch. The slots 44 of the present cutter 22 are also generally at least about 0.025 inch in axial length along the longitudinal axis of the body 30. One skilled in the art will readily appreciate that the slots 44 of the present cutter 22 can be varied in axial length to vary the length of the cantilevered arm 43 that connects the flanges 42 to the cutter 22. The slots 44, and the arm 43 defined between the slots 44, and the tangs, allow radial inward compression of the flanges 42 and spring arms 43, or tangs, to ease assembly of the cutter 22 within the cutter housing 21 as described below.

Desirably, the cutter 22, and especially the portion containing the slots 44, is made of a material having an adequate spring constant as will be understood by those of skill in the art. In one embodiment, the cutter 22 is made from a medical grade stainless steel alloy. The chosen material preferably has characteristics including the ability to allow the cantilevered spring arm 43 to deflect radially inwardly an adequate distance over the length of the arm 43 without exceeding the elastic limit of the material (i.e., the deflection is an elastic deformation). As is known, elastic deformations allow structures to deflect and substantially return to their initial shape or position. For instance, special hardening methods may be used to maintain the elasticity of the selected material in the deflection range necessary for a specific application.

With reference now to FIG. 2, the cutter 22 is snap fit into the cutter housing 21. Advantageously, the arms 43 may be deflected radially inward such that the cutter 22 may be inserted into the cutter housing 21 through an aperture or lumen having a smaller ID than the inside diameter of the retaining groove 54 of the cutter housing 21. Preferably, the cutter 22 is inserted from the distal end of the housing 21 and slid proximally through the housing 21 until the flanges 42 snap outward into the race 54. Thus, the cutter 22 will be retained in this housing even if it separates from its drive element 24. Desirably, the arms 43 substantially return to their original, relaxed positions within the retaining groove 54 the cutter housing 21 following installation. It should be appreciated that the arms 43 may also be maintained under a slight bending stress (i.e., the inside diameter of the race 54 may be smaller than the outside diameter about the relaxed flanges 42) if desired.

Figure 7:
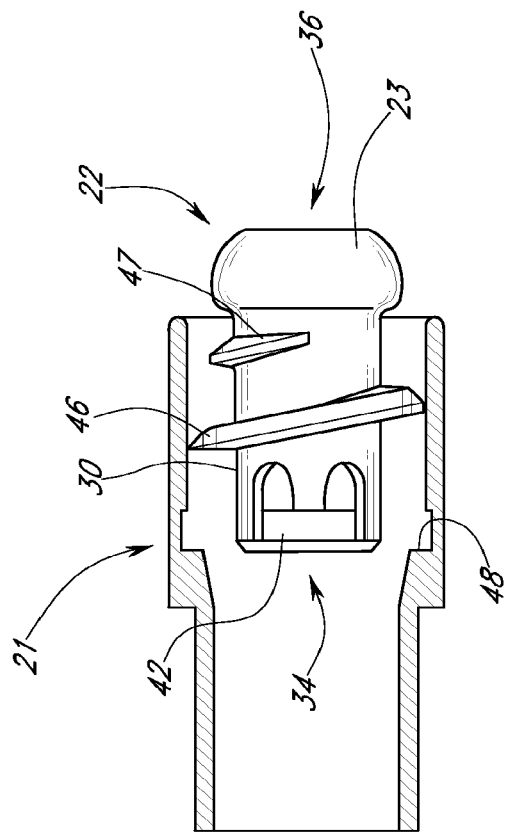
FIG. 7 is a partially sectioned side view of a further cutter and housing.

With reference now to FIGS. 2 7, an external element for cutting or manipulating occlusions, such as thrombus, will be described in detail. The element may include a thread 46 that extends along a portion of the exterior surface of the body 30 of the present cutter 22. The thread 46 preferably extends distally from a location on the body 30 that is distal to the connector 40. The thread 46 may be manufactured using any suitable technique well known to those of skill in the art.

In one embodiment having a cutter housing 21 with an inside diameter of about 0.0685 inch, the major diameter of the thread 46 is approximately 0.0681 inch. However, the major diameter of the present thread 46 may range from about 0.050 inch to about 0.130 inch or otherwise, depending upon both the inner diameter of the cutter housing and the intended clinical application. The thread 46 of the foregoing embodiment has a pitch of approximately 0.0304 inch and is desirably helical. The pitch may range from about 0.005 inch to about 0.060 inch, and may be constant or variable along the axial length of the cutter 22. The thickness of the present thread 46 in the axial direction is approximately 0.008 inch; however, the thickness may range from about 0.003 to about 0.05, and may be constant or variable along the length of the thread 46. Thus, it is anticipated that the cutters 22 may also have a generally spiral helix thread.

In some of the illustrated embodiments, the thread 46 extends approximately two complete revolutions around the cylindrical body 30. The thread 46 may be a continuous radially outwardly extending ridge as illustrated, or may comprise a plurality of radially outstanding blades or projections preferably arranged in a helical pattern. The thread 46 may extend as little as about one-half to one full revolution around the cutter body 30, or may extend as many as 2½ or 3 or more full revolutions around the circumference of the body 30, as is discussed more below. Optimization of the length of the thread 46 may be accomplished through routine experimentation in view of the desired clinical objectives, including the desired maneuverability (i.e., tractability through tortuous anatomy) and the length of the cutter 22, as well as the nature of the cutting and/or aspiration action to be accomplished or facilitated by the cutter 22. In addition, while the present cutter 22 is illustrated and described as having a single thread, one skilled in the art will appreciate that the cutter 22 may also have multiple threads, a discontinuous thread or no threads.

Figure 6:
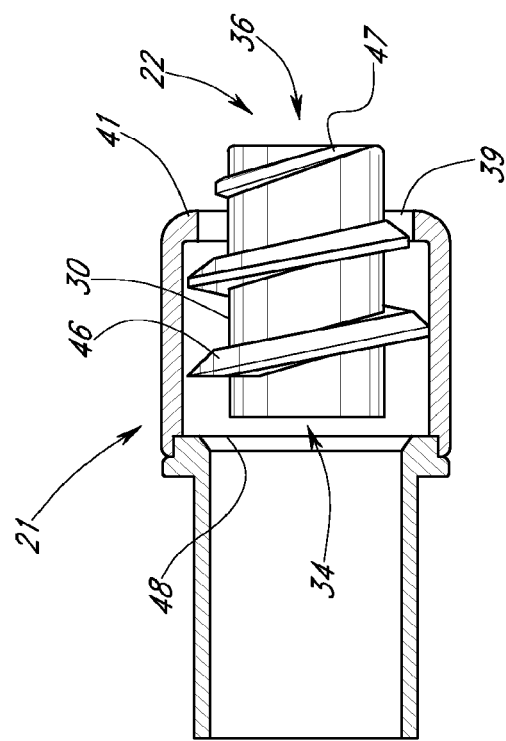
FIG. 6 is a partially sectioned side view of yet another cutter and housing.

Referring now to FIGS. 6 and 7, the thread 46 illustrated therein is a constant pitch and varies in cross-section along its length from a relatively low profile at the distal end 36 to a relatively higher profile at the proximal end 34 of the cutter tip 22. Such a ramped thread 46 improves performance when the catheter encounters more dense obstructive material. In such an embodiment, the major diameter of the distal lead 47 of the thread 46 is smaller than the major diameter of the thread along the more proximal portions of the cutter shaft 30. It is anticipated that the pitch of the thread 46 may also vary along with the profile of the thread 46 to alter the clinical effects accomplished.

As discussed directly above, the pitch of the thread 46 may also be varied along the axial length of the cutter body 30. Varying the pitch allows a modified function at different points along the axial length of the cutter 22, such as a greater axial thread spacing at the distal end 36 of the cutter 22 to engage material and a relatively closer axial spacing of the threads at the proximal end 34 of the cutter 22 for processing the material. In general, the pitch may range from about 0.010 inch at the distal end to about 0.080 inch at the proximal end. In one embodiment, the pitch at the distal end 36 is approximately 0.034, the pitch at the proximal end 34 is approximately 0.054, and the pitch varies continuously therebetween. The maximum and minimum pitch, together with the rate of change of the pitch between the proximal end 34 and the distal end 36 can be optimized through routine experimentation by those of skill in the art in view of the disclosure herein.

With reference to FIG. 6, the ramped thread diameter results in a distal portion 36 of the cutter 22 that can extend distally beyond the cutter housing 21 and a proximal portion 34 of the cutter tip 22 that will be retained within the cutter housing 21. This results, in part, from a radially inwardly extending retaining flange 41 which reduces the diameter of the opening 39 at a distal end 52 of the cutter housing 21 relative to an internal bore of the housing 21. As shown in FIG. 3, the distal portion 45 of the thread 46 may have its leading edge broken, chamfered or rounded to remove a sharp corner or edge. By eliminating the sharp corner or edge, the risk of accidental damage to the patient is reduced. The distal edge of the cylindrical body 30 and the flanges 42 may also be broken, chamfered or otherwise rounded to eliminate or reduce sharp edges.

With reference to FIG. 2, the outside diameter of the thread 46 in this embodiment has a close sliding fit with the inside diameter, or inner wall, of the cutter housing 21. In this configuration, the atheromatous material will be avulsed by the threads 46, fed further into the housing 21 toward the flanges 42 and chopped or minced by the flanges 42. To further enhance the chopping or mincing action of the flanges 42, a stationary member (not shown) or a set of stationary members (see, e.g., on FIGS. 21 and 22) may be positioned such that the rotating flanges 42 and the stationary member or members (not shown) effect a shearing action. The shearing action breaks up the strands into shorter sections, which are less likely to clog the instrument, as described below. Moreover, the flanges 42 may be provided with sharply chamfered leading or trailing edges to alter their cutting action, if desired.

It may be desirable in some embodiments to provide an annular space between the outside diameter of the thread 46 and the inside diameter of the cutter housing 21. By spacing the thread 46 apart from the inside wall of the central lumen 20, an annular space is provided for material to pass through the cutter housing 21 without being severed by the thread 46 of the cutter tip 22. This may be utilized in conjunction with vacuum, discussed below, to aspirate material into the atherectomy device without the necessity of complete cutting by the thread 46 or flanges 42. This may be advantageous if the rate of material removal effected by aspiration is higher than the rate at which material removal may occur with the thread 46 engaging such material. In addition, the rotational atherectomy device 10 may more readily aspirate certain lesion morphologies, such as those including portions of calcified plaque, if the thread 46 is not required to cut all the way through the aspirated material. In general, the desired radial distance between the thread 46 and the inside wall of the cutter housing 21 will be between about 0.0001 inch and about 0.008 inch, to be optimized in view of the desired performance characteristics of the particular embodiment. In an embodiment intended solely to aspirate soft atheromas, the cutting function of the thread 46, or the thread 46 itself, may be deleted entirely, so that cutting occurs by the flanges or cutting blocks 42 and/or stationary members (not shown) in cooperation with the aspiration provided by a vacuum source.

Interventions for which an atraumatic distal tip is desired, such as, for example but without limitation, saphenous vein graphs, can be well served by an atraumatically tipped cutter 22, as illustrated in FIG. 7. The blunt tip cutter 22 preferably has a bulbous or rounded tip 23 that extends from the distal end of the cutter 22. The tip 23 preferably has a radially symmetrical configuration such that upon rotation it presents a smooth, atraumatic surface for tissue contact. Viewed in side elevation, such as in FIG. 7, the tip 23 may have a generally hemispherical, oval, elliptical, aspheric or other smooth curve on its radial surface with either a curved or truncated (i.e., flat) distal surface. As will be recognized, the shape of the tip 23 may be varied to achieve desirable effects on the catheter crossing profile or on soft atheromas, etc. In general, the tip 23 advantageously minimizes the possibility of traumatic contact between the healthy wall of the vessel and the thread 46 or other cutting element.

The outside diameter of the tip 23 may range from the outside diameter of the cutter body 30 to the outside diameter of the cutter housing 21. Diameters greater than the housing 21 may also be used, but diameters smaller than the housing 21 facilitate a smaller crossing profile of the instrument 10. The axial length of the tip 23 may be varied to suit the intended application, but will generally be within the range of from about 0.050 inch to about 0.100 inch in a coronary artery application.

The outside surface of tip 23 may be provided with surface texturing or treatments. As will be recognized by those of skill in the art, the surface texturing or treatments may be formed by abrasive coating (i.e., coating the tip with diamond particles), acid etching or any other suitable method. The texture or treatments may be on the distal surface or the lateral surfaces or both such that a two-stage interaction with the encountered materials may occur. Thus, the tip can be used for grinding or otherwise remodeling the encountered materials. For example, an abrasive distal surface can be used to cut through calcified plaque, while a smooth radial surface can compress soft material against the vessel wall to facilitate acceptance into the helical thread 46 of the cutter 22. Varying the distance between the distal end 47 of the thread 46 and the proximal end of the tip 23, as well as varying its geometry, can allow adjustments to the cutter aggressiveness. For instance, the thread 46 may extend up to the proximal edge of the tip 23 and allow early engagement of the encountered materials relative to a cutter 22 having a length of unthreaded shaft between the proximal edge of the tip 23 and the distal end 47 of the thread 46.

The tip 23 can be integrally formed with the cutter tip 22, such as by machining techniques known in the art. Alternatively, it can be separately formed and secured thereto, such as by soldering, adhesives, mechanical interference fit, threaded engagement and the like. The tip can be machined from a suitable metal or molded or otherwise formed from a suitable polymeric material such as polyethylene, nylon, PTFE or others known to those of ordinary skill in the art.

Moreover, the cutter tip 22 itself may be machined such that the distal facing end is serrated or discontinuously formed. The discontinuous thread may comprise a number of inclined surfaces forming distally facing teeth. In such cutters, the cutter is more aggressive in the forward direction. With reference to FIG. 8A-8C, such a cutter tip 22 may have serrations 57 formed along the distal end 47 of the thread 46. The serrations may also be positioned on an extended nose portion (not shown) of the cutter. The serrations 57 preferably are formed to extend outward radially from the center axis of the cutter 22. While the illustrated serrations 57 are formed in a straight line, the serrations 57 may also be arcuate in shape to form a sickle-shaped cutting surface. The illustrated serrations 57 preferably have a depth of between about 0.0005 inch and about 0.0040. More preferably, the serrations 57 are about 0.0020 deep. The serrations 57 also preferably are formed with a sloping face 59 that is at an angle 1 of between about 45☐ and about 85☐ with a longitudinal plane that extends through the axis of rotation. In a presently preferred arrangement, the sloping face extends at an angle of about 60☐ relative to the same plane. Moreover, the run of the sloping face 59 is preferably between about 0.0020 inch and about 0.0050 inch. In the preferred arrangement, the run is about 0.0035 inch in length. The serrations in the illustrated cutter extend over only a forward facing portion 45 of the distal end 36 of the cutter 22; however, it is anticipated that the cutter 22 may also comprise a serrated thread that extends the entire length of the thread 46.

In many interventions, it is desirable to have the cutter 22 floating axially within the housing 21. FIG. 6 illustrates a cutter 22 arranged to float axially within the housing 21. Preferably, in such configurations, the cutter 22 is provided with an anti-locking thread design. For instance, the thread 46 may be configured such that it cannot jam within the housing 21 at either extreme of axial travel. Such a configuration may involve having a minimum thread major diameter which is greater than the diameter of the opening in the distal end of the device 10 or having a pitch which is less than the thickness of the ring flange 41 formed at the distal tip of the cutter housing 21. Other configurations may also be readily apparent to those of ordinary skill in the art. The axial travel and the thread design desirably cooperate to allow the cutter 22 to self-adjust to digest soft fibrous material.

The housing 21 may conveniently be assembled from two pieces, to entrap the cutter 22 therein. The two pieces are then laser-welded or otherwise secured together. In one embodiment, the housing 21 may be split longitudinally, the cutter 22 inserted, and the two pieces may then be secured together. In another presently preferred embodiment, the two pieces may split the housing 21 into a distal component and a proximal component (see FIG. 6). The two components may be assembled to trap the cutter 22 therein and may then be laser-welded or otherwise secured together. Such assemblies allow for the cutter 22 to be captured within the cutter housing 21 as well as allow for certain relatively loose manufacturing tolerances for the cutter 22 and the cutter housing 21 such as will reduce manufacturing costs. Such assemblies also enable better fits because the flanges 42 require less travel (i.e., the flanges 42 do not require deflection for insertion into the housing 21).

Desirably the cutter 22 is positively retained in the cutter housing 21 for rotation, as discussed directly above. With reference again to FIG. 2, the illustrated housing 21 internally may be a stepped cylinder having a proximal end 50 and the distal end 52. In some embodiments featuring axial movement of the cutter 22 relative to the cutter housing 21 or tubular body 12, an annular bearing surface 48 (see FIG. 6) provides a proximal limit of travel for the flanges 42 on cutter 22. Notably, the annular bearing surface 48 may be formed within the cutter housing 22 (as illustrated in FIG. 6) or within the tubular body 12 (not shown).

In a specific coronary artery embodiment, the internal diameter of the distal portion 52 of the cutter housing 21 is approximately 0.0689 inch and may range from about 0.050 inch to about 0.150 inch. The proximal end 50 of the present cutter housing 21 preferably has an internal diameter of approximately 0.0558 inch. The internal diameter 50 of the proximal end of the present cutter housing 21 may range from about 0.035 inch to about 0.130 inch. At its distal end 52, the cutter housing 21 may be provided with a radially inwardly extending retaining lip, such as flange 41 in FIG. 6, sized and configured such that the cutter 22 is captured within the cutter housing 21 and such that the cutter 22 cannot screw itself out of its captured position within the cutter housing 21.

The exterior diameter of the distal end 52 of the cutter housing 21 in one embodiment is approximately 0.0790 inch; however, the distal exterior diameter may range from about 0.039 inch to about 0.150 inch depending upon cutter design and the intended clinical application. The distal portion 52 of the cutter housing 21 in the illustrated embodiment is about 0.117 inch in length but the length may vary from about 0.020 inch to about 0.50 inch. In the embodiment illustrated in FIG. 2, the outside diameter of the proximal portion 50 of the cutter housing 21 may be less than the diameter of the distal portion 52 to produce an annular shoulder 51 to limit concentric proximal advance of the proximal section within the tubular body 12. The proximal section of the housing 50 extends axially for approximately 0.09 inch but its length may vary as will be understood by those of skill in the art.

In general, the cutter housing 21 may be integrally formed or separately formed and secured to the distal end 16 of the tubular body 12 in accordance with any of a variety of techniques which will be known to those of skill in the art. The concentric overlapping joint illustrated in FIG. 2 can be utilized with any of a variety of secondary retention techniques, such as soldering, the use of adhesives, solvent bonding, crimping, swaging or thermal bonding. Alternatively, or in conjunction with any of the foregoing, an outer tubular sleeve (not shown) may be heat shrunk over the joint between the cutter housing 21 and the tubular body 12. While not shown, it is presently preferred to slide the proximal end 50 of the cutter housing 21 over the distal end 16 of the tubular body 12 and apply a fillet of adhesive about the proximal extremity of the cutter housing 21 to hold the two components together. In such a configuration, the proximal portion 50 of the cutter housing 21 desirably does not block a portion of the annual recess defined between the central lumen 20 and the outer surface of the drive element 24. It is anticipated that this style of connection can be utilized with any of the cutter housing features described herein and that the cutter housing 21 may be provided with an internal stop to limit axial displacement of the cutter housing 21 relative to the distal end 16 of the tubular body 12.

With reference again to FIG. 2, at the proximal interior end of the distal component 52 of the housing 21 is the shallow outwardly extending annular retaining race or groove 54 introduced above. The retaining race 54 in one embodiment is approximately 0.0015 inch deep relative to the inner diameter of the distal section 52 and may range in depth from about 0.0005 inch to about 0.020 inch. The retaining race 54 in the illustrated embodiment is about 0.0135 inch in axial width; however, as one skilled in the art will readily appreciate, the race width may be varied and still accomplish its retention function as is discussed further below. Moreover, the race 54 may be located proximally, or extend proximally, of the cutter housing 21 such that the cutter 22 may be retracted within the tubular body 12.

The retaining race 54 cooperates with the flanges 42 of the present cutter 22 to retain the cutter 22 within the cutter housing 21 as described in detail above. The flanges 42 provide a bearing surface for the cutter 22 to facilitate rotational movement of the cutter 22 relative to the housing 21. In addition, where the axial dimensions of the flanges 42 and the race 54 are approximately the same, the cutter 22 may be substantially restrained from axial movement within the cutter housing 21. As will be appreciated, the race 54 may be larger in axial width relative to the thickness of the flanges 42 to allow axial movement of the cutter 22 within the cutter housing 21 or even into the tubular body 12 as discussed above.

With continued reference to FIG. 2, the distal extremity of the illustrated cutter 22 may be approximately aligned with the distal extremity of the cutter housing 21. As such, the length of the cutter housing 21 distal of the retaining groove 54 substantially corresponds to the length of the portion of the of the cutter 22 which extends distally of the distal surfaces of flanges 42. By creating a substantially flush positioning at the distal end 52 of the cutter housing 21 and the cutter 22, the possibility of accidental damage to the intima by the cutter 22 is reduced. One skilled in the art will readily recognize, however, that the distal end 36 of the cutter 22 may alternatively extend beyond, or be recessed within, the distal end 52 of the cutter housing 21 (i.e., the embodiment of FIG. 7). Additionally, the cutter 22 may be arranged for selective extension and retraction relative to the cutter housing 21, the benefits of which are described below.

Another cutter 60 and associated cutter housing 70 are illustrated in FIGS. 5A and 5B. Although the cutter 60 embodies many of the same features as the cutter 22 described above, like elements will generally be called out by new reference numerals for ease of discussion. It should be recognized, however, that any of the features, aspects or advantages of the cutter 22 described above and the cutter 60 described below may be easily interchanged by one of ordinary skill in the art.

The cutter 60 is preferably symmetrical about the rotational axis having a body 61 with an annular retention structure, such as a retaining race 62, located near the body's proximal end 64. The retaining race 62, or connector portion, in the illustrated embodiment is about 0.007 inch deep, and about 0.008 inch wide, although both dimensions can be varied as may be desired and still achieve the desired retention function, as will be readily recognized by one with skill in the art. Proximal to the retaining race 62, the outside diameter of the body 61 is rounded or tapers from about 0.04 inch to about 0.036 inch. Preferably, all edges are broken, chamfered or otherwise rounded to ensure burr free and dull corners and to facilitate assembly. The cutter 60 may also have a thread 66 similar to that described above.

The cutter 60 is preferably snap fit into the cutter housing 70 by inserting the cutter 60 into the distal end 74 of the cutter housing 70. The cutter housing 70 is preferably similar to that described above with the exception that the retaining race 54 of the first housing is replaced by a set of inwardly extending radial retaining members 72. With reference to FIG. 5B, the present cutter housing 70 has three retaining members 72, preferably circumferentially symmetrically distributed (i.e., on about 120∞ centers). One skilled in the art will recognize that the number, size and shape of the retaining members can vary; at least two will generally be used to achieve opposition, and embodiments having 3, 4, 5 or more may be readily utilized. It is possible, however, to utilize a single retaining member in some applications such that the single retaining member operates as a stationary cutter member either with or without a set of cutter blocks (42 in the embodiments described above).

As with the arms 43 above, the retaining members 72 are sized and configured to allow deflection within the elastic range such that the retaining members 72 may be deflected and inserted into the race 62 as discussed below. Again, this snap fit configuration advantageously enables the cutter 60 to be retained in the cutter housing 70 even if the cutter 60 separates from the driving element (not illustrated).

As introduced directly above, the retaining members 72 may serve the added function of stationary cutting members. As such the retaining members 72 may be sized accordingly. The illustrated retaining members 72 are about 0.007 inch thick in the axial direction; however, one skilled in the art will appreciate that the thickness can range from about 0.003 inch to about 0.030 inch or otherwise depending upon material choice and the desired degree of axial restraint. The retaining members 72 extend about 0.007 inch inward from the interior wall of the cylindrical cutter housing 70. The retaining member 72 length can vary, however, depending upon the desired dimensions of the cutter housing 70 and the cutter 60. As shown in FIG. 5B, the side edges 73 of the retaining members 72 may be provided with a radius such that the radial interior and exterior ends are wider than the central portion. Additionally, while shown with a concave radius, the stationary retaining members 72 may alternatively be provided with a convex radius (not shown) to form a smoothly transitioning profile.

As one skilled in the art will appreciate, the retaining members 72 are provided to engage within the retaining race 62 of the cutter 60. The retaining members 72 and the race 62 may be sized and configured such that the cutter 60 is either substantially restrained from axial movement relative to the cutter housing 70 or some axial travel is allowed between the two components. The retaining members 72 may also provide a bearing surface for the rotational movement of the cutter 60 relative to the cutter housing 70. For instance, the race 62 of the cutter 60 desirably rides on the ends of the retaining members 72 such that the retaining members 72 provide bearing surfaces at their inner most edges and allow the cutter 60 to be rotated relative to the housing 70. Similar to the assembly described above, the distal end 65 of the cutter 60 may be approximately flush with the distal end 74 of the cutter housing 70. Alternatively, the distal end 65 of the cutter 60 may extend distally from or may be slightly recessed within the distal end 74 of the cutter housing 70 by as much or more than is shown in FIG. 5A. Moreover, in specific applications, the cutter 60 may be selectively advanced or retracted relative to the cutter housing 70, enabling advantages that are described below.

With reference again to FIG. 2, the distal end of a flexible drive shaft 24 may be firmly secured within an axial bore 32 of the cutter 22. The cutter 22 may be secured to the flexible drive shaft 24 by any of a variety of ways such as crimping, swaging, soldering, interference fit structures, and/or threaded engagement as will be apparent to those of skill in the art. Alternatively, the flexible drive shaft 24 could extend axially through the cutter 22 and be secured at the distal end 36 of the cutter 22.

In any of the embodiments described herein, the cutter 22 and the cutter housing 21 may be designed so that the cutter 22 may be positioned within the cutter housing 21 in a manner that allows axial movement of the cutter 22 relative to the cutter housing 21. Controllable axial movement of the cutter 22 may be accomplished in a variety of ways, to achieve various desired clinical objectives. For example, in either of the embodiments illustrated in FIGS. 2 and 5a, a minor amount of axial movement can be achieved by increasing the axial dimension of the annular recesses 54, 62 with respect to the axial dimension of the flanges 42, or retaining members 72. The annular proximal stop 48 (FIG. 2) can be effectively moved proximally along the tubular body 12 to a position, for example, within the range of from about 5 centimeters from the distal end 52 to at least about 10 or 20 centimeters from the distal end 52. This permits increased lateral flexibility in the distal 10 cm or 20 cm or greater section of the tubular body 12. Alternatively, the proximal stop 48 can be eliminated entirely such that the entire inside diameter of the tubular body 12 is able to accommodate the flanges 42 or their structural equivalent, or the outside diameter of the thread 46, depending upon the embodiment. Limited axial movement can also be accomplished in the manner illustrated in FIGS. 6 and 7, as will be appreciated by those of skill in the art.

In general, relatively minor degrees of axial movement, such as on the order of about one or two millimeters or less may be desirable to help reduce the incidence of clogging and also reduce trauma, such as by the distal cutting tip pressing against a vessel wall. Minor axial movability can also help compensate for differential elongation or compression between the tubular body 12 and the drive shaft 24.

A greater degree of axial movability may be desirable in embodiments in which the cutter 22 may be controllably extended partially beyond the housing 21 such as to improve engagement with hard obstructive material. Retraction of the cutter 22 within the cutter housing 21 may be desirable during insertion of the device 10, to minimize trauma to the vascular intima during positioning of the device 10. The cutter 22 may thereafter be advanced distally on the order of 1 to 3 or 5 millimeters beyond the distal end 52 of the housing 21, such as to engage obstructive material to be drawn into the cutter housing 21.

More significant proximal retraction of the cutter 22 within the housing 21, such as on the order of 5 to 20 centimeters from the distal end 52, may be advantageous during positioning of the atherectomy catheter. As is understood in the art, one of the limitations on positioning of a translumenal medical device within tortuous vascular anatomy, particularly such as that which might be encountered in the heart and intracranial space, is the lateral flexibility of the distal portion of the device. Even if the outside diameter or crossing profile of the device is small enough to reach the stenotic region, the device still must have sufficient pushability and sufficient lateral flexibility to navigate the tortuous anatomy.

In the context of rotational atherectomy catheters, the rotatable drive shaft 24, as well as the cutter 22, can significantly increase the rigidity of the catheter. In accordance with the present invention, the drive shaft 24 and the cutter 22 may be proximally withdrawn within the tubular housing 12 to provide a relatively highly flexible distal catheter section that is capable of tracking a guidewire 28 through tortuous vascular anatomy. Once the outer tubular housing 12 of the atherectomy catheter has been advanced to the treatment site, the cutter 22 and the drive shaft 24 may be distally advanced through the tubular body 12 and into position at the distal end 16. In this manner, the rotational atherectomy catheter can be positioned at anatomical locations that are not reachable if the drive shaft 28 and housing 21 at the distal end 16 of the tubular body 12 are advanced as a single unit.

In general, the cutter 22 is preferably proximally retractable from the distal end 52 of the cutter housing 21 by a distance sufficient to permit the outer tubular body 12 and cutter housing 21 to be positioned at the desired treatment site. In the context of coronary artery disease, the distance between the distal end 52 of the cutter housing 21 and the retracted cutter 22 is generally be within the range of from about 5 cm to about 30 cm and preferably at least about 10 cm. Proximal retraction of the cutter 22 over distances on that order will normally be sufficient for most coronary artery applications.

The flexible drive shaft 24 is preferably a hollow, laminated flexible "torque tube" such as may be fabricated from an inner thin-wall polymeric tubing, an intermediate layer of braided or woven wire, and an outer polymeric layer. In one embodiment, the torque tube comprises a polyimide tube having a wall thickness of about 0.004 inch, with a layer of braided 0.0015 inch stainless steel wire embedded therein. The laminated construction advantageously produces a tube with a very high torsional stiffness and sufficient tensile strength, but which is generally laterally flexible. However, depending upon the desired torque transmission, diameter and flexibility, any of a variety of other materials and constructions may also be used. In general, the drive shaft 24 should have sufficient torsional rigidity to drive the cutter 22 through reasonably foreseeable blockages. It is also recognized that in some applications, the drive shaft 24 may be a wire or other solid construction such that no inner lumen 26 extends therethrough.

The outside diameter of one embodiment of the present hollow flexible drive shaft 24 is approximately 0.032 inch, but may range between about 0.020 inch and about 0.034 inch or more. One skilled in the art will appreciate that the diameter of the flexible drive shaft 24 may be limited by a minimum torsional strength and a guidewire diameter, if a guidewire 28 is present, at the low end, and maximum permissible catheter outside diameter at the high end.

The selection of a hollow drive shaft 24 allows the device 10 to be advanced over a conventional spring-tipped guidewire 28, and preferably still leaves room for saline solution, drugs or contrast media to flow through the lumen 26 of the drive shaft 24 and out of the distal opening 39 on the cutter 22. The internal diameter of the present hollow flexible drive shaft 24 is thus partially dependent upon the diameter of the guidewire 28 over which the flexible drive shaft 24 must track. For example, the internal diameter of the guidewire lumen 26 in one embodiment of the present hollow flexible drive shaft 24, intended for use with a 0.018 inch diameter guidewire, is approximately 0.024 inch. Because the flexible drive shaft 24 preferably extends between the control 18 and the cutter 22, the length of the present hollow flexible drive shaft 24 should be sufficient to allow the cutter assembly to reach the target location while also allowing adequate length outside of the patient for the clinician to manipulate the instrument 10.

With reference again to FIG. 2, the lumen 20 of the assembled device 10 is thus an annular space defined between the inside wall of the flexible tubular body 12 and the outside of the flexible drive shaft 24. This lumen 20 may be used to aspirate fluid and material from the cutter. Preferably, sufficient clearance is maintained between the tubular body 12 and the rotating drive shaft 24 to minimize the likelihood of binding or clogging by material aspirated from the treatment site.

In general, the cross-sectional area of the lumen 20 is preferably maximized as a percentage of the outside diameter of the tubular body 12. This permits an optimization of lumen cross-sectional area which maintains a minimal outside diameter for tubular body 12, while at the same time permitting an acceptable flow rate of material through the aspiration lumen 20, with minimal likelihood of clogging or binding which would interrupt the procedure. Cross-sectional area of the aspiration lumen 20 thus may be optimized if the drive tube 24 is constructed to have relatively high torque transmission per unit wall thickness such as in the constructions described above. In one embodiment of the invention, intended for coronary artery applications, the outside diameter of tubular body 12 is about 0.080 inch, the wall thickness of tubular body 12 is about 0.008 inch, and the outside diameter of the drive shaft 24 is about 0.031 inch. Such a construction produces a cross-sectional area of the available aspiration portion of central lumen 20 of about 0.00245 square inch. This is approximately 50% of the total cross-sectional area of the tubular body 12. Preferably, the cross-sectional area of the lumen 20 is at least about 25%, more preferably at least about 40%, and optimally at least about 60% of the total cross-sectional area of the tubular body 12.

The tubular body 12 may comprise any of a variety of constructions, such as a multi-layer torque tube. Alternatively, any of a variety of conventional catheter shaft materials such as stainless steel, or single layer polymeric extrusions of polyethylenes, polyethylene terephthalate, nylon and others well known in the art can be used. In one embodiment, for example, the tubular body 12 is a PEBAX extrusion having an outside diameter of approximately 0.090 inch. However, the outer diameter can vary between about 0.056 inch for coronary vascular applications and about 0.150 inch for peripheral vascular applications. Also, because the tubular body 12 must resist collapse under reasonably anticipated vacuum forces, the foregoing tubular body 12 desirably has a wall thickness of at least about 0.005 inch. The wall thickness can, however, be varied depending upon materials and design.

The distal end of the tubular body 12 may be affixed to the proximal end 50 of the cutter housing 21 as shown in FIG. 2 and described above. The proximal end of the tubular body 12 may be affixed to the control 18 as described below.

Figure 9:
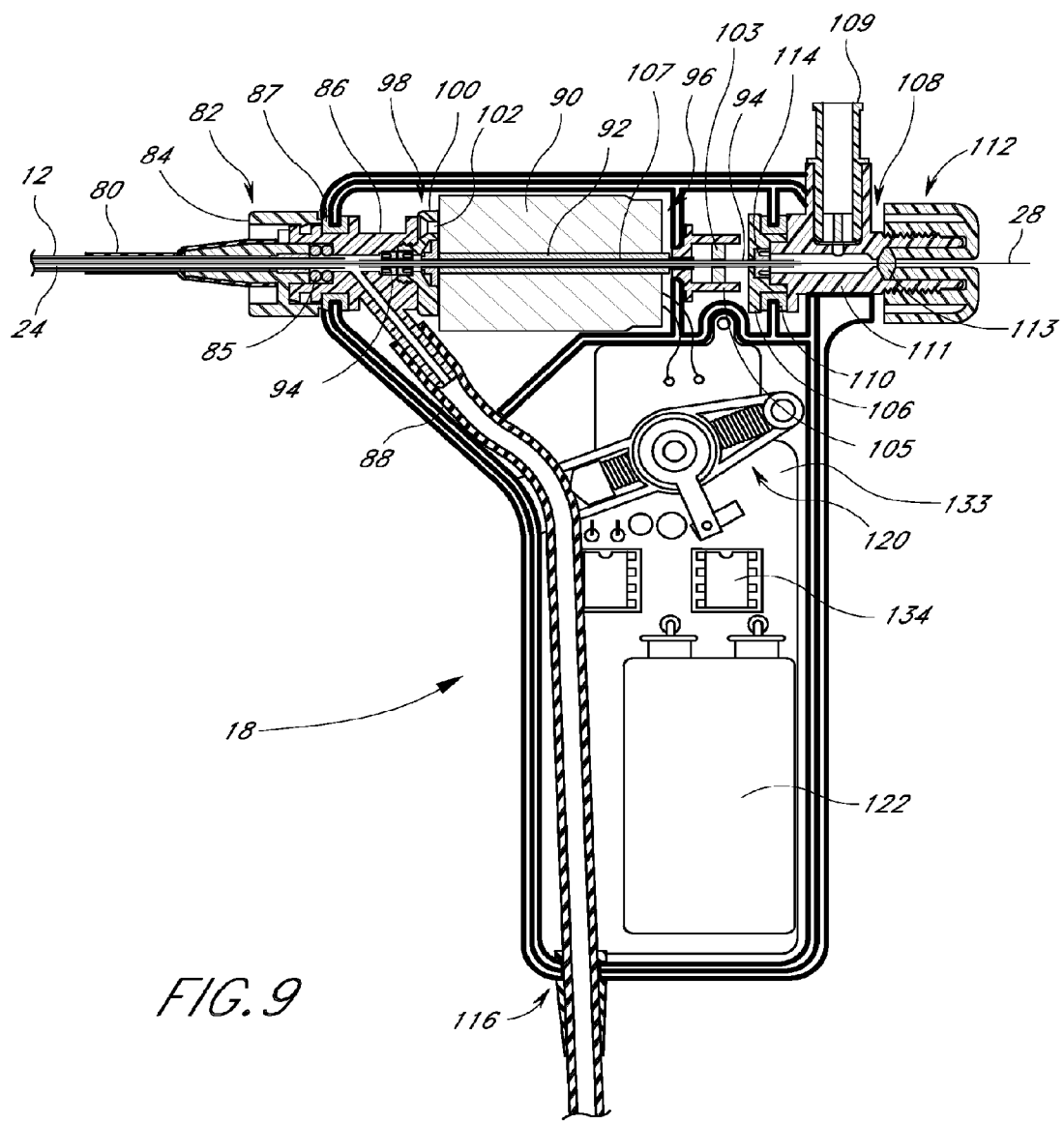
FIG. 9 is a sectioned side view of a control having features, aspects and advantages in accordance with the present invention.

With reference to FIG. 9, the point at which the flexible drive shaft 24 is connected to the control 18 is a likely point of damaging bending forces. As such, a reinforcing tube 80 is desirably provided to reduce the likelihood of a failure at that location due to bending forces. The reinforcing tube 80 may extend from the control unit 18 along a proximal portion of the tubular body 12. The reinforcing tube 80 preferably extends distally over the tubular body 12 at least about 3 cm and more preferably about 6 cm, and desirably comprises silicone or other conventional biocompatible polymeric material. The illustrated reinforcing tube 80 provides support to avoid over bending and kinking at the proximal end of the drive shaft 24. With continued reference to FIG. 9, the reinforcing tube 80 may be fastened to the control 18 such as by interference fit over a snap tip assembly 82 through which the flexible drive shaft 24 and tubular body 12 enter the control 18. Thus, the reinforcing tube 80 advantageously envelops a proximal portion of the tubular body 12.

Respectively, the flexible drive shaft 24 and the tubular body 12 operatively connect the cutter 22 and the cutter housing 21 to the control 18 of the illustrated embodiment. With continued reference to FIG. 9, the tubular body 12 and the drive shaft 24 enter the control 18 through the snap tip assembly 82. The snap tip assembly 82 may be provided with a connector, such as a hub 84, having a central lumen in communication with a vacuum manifold 86. The tubular body 12 may be connected to the hub 84. Specifically, the hub 84 may snap onto and seal a vacuum manifold 86 to the hub 84 and, consequently, to the tubular body 12. The hub material, therefore, desirably provides long-term memory for snap-fit tabs that secure this part to the rest of the assembly. The presently preferred hub 84 is injection molded using a white acetyl such as Delrin. The hub 84 may be rotatable, and may enable the operator to rotate the tubular body 12 relative to the control 18 such that the operator, or clinician, may steer the tubular body 12 without having to move the control 18 along with the tubular body 12. Friction to limit this rotation may be provided by a bushing 87 that is compressed against the hub 84 in the illustrated embodiment.

The tubular body 12 may be reinforced internally where it passes through the hub 84, such as by a thin-wall stainless steel tube (not shown) that extends through and is bonded to the hub 84. In general, a good rotational coupling is desired between the tubular body 12 and the hub. In one embodiment, a portion of the hub bore may be hexagonal shaped, or formed in any other non-circular shape which corresponds to a complementary shape on the tube to enhance the rotational connection between the hub bore and the tube (not shown). Epoxy or other adhesives (not shown) may also be injected into a space around the stainless steel tube to help prevent the stainless steel tube (not shown) from rotating relative to the hub 84. The adhesive also advantageously secures the two components such that the tube (not shown) is less likely to axially pull out of the hub 84.

With continued reference to FIG. 9, the vacuum manifold 86 is preferably fastened to a vacuum hose 88 at one outlet and to a motor 90 at a second outlet. The hub-end of the vacuum manifold 86 desirably houses two silicone rubber O-rings 85 that function as dynamic (rotatable) seals between the manifold 86 and the steel tube (not shown) which extends through the hub 84. The opposite end of the manifold 86, near the proximal end of the drive tube 24, preferably contains a pair of butyl rubber fluid seals 94. These dynamic fluid seals 94 may be lubricated with silicone grease. The two fluid seals 94 are mounted back-to-back, with their lips pointing away from each other. In this configuration, the distal seal (i.e., closest to the cutter 22) protects against positive pressure leaks such as may be caused by blood pressure and the proximal seal (i.e., closest to the motor 90) excludes air when the system is evacuated and the pressure outside the instrument 10 is higher than the pressure inside the instrument 10.

The vacuum manifold 86 may be connected to the motor 90 through use of a threaded motor face plate 100. The vacuum manifold 86 is preferably threaded onto the face plate 100 but may be connected in any suitable manner. The face plate 100 may be attached to the output end of the motor 90 by a threaded fastener 102. The presently preferred motor 90 is a modified 6-volt direct-current hollow-shaft, 22 mm outside diameter motor built by MicroMo.

In the illustrated embodiment, power is transmitted from the motor 90 to the flexible drive shaft 24 by a length of medium-wall stainless steel tubing that is preferably adhesively-bonded to the drive shaft 24. The tubing forms a transfer shaft 107 and is preferably coated on the outer surface with approximately 0.001 inch of Type-S Teflon. The Teflon-coated, exposed ends of the rigid drive shaft, or transfer shaft 107, provide a smooth wear-surface for the dynamic fluid seals discussed above. The transfer shaft tubing may be hypodermic needle stock measuring approximately 0.036 inch inside diameter by 0.053 inch outside diameter, before coating. The transfer shaft 107 desirably is slip fit through the approximately 0.058 inch inside diameter of the hollow motor shaft, and desirably extends beyond the length of the motor shaft in both directions. The slip fit advantageously accommodates axial sliding movement of the transfer shaft 107 relative to the motor 90 and the balance of the instrument 10. Thus, axial movability may be accommodated.

The drive shaft 24 is advantageously capable of axial movement relative to the motor 90 as described above. Controlled axial movement of the drive shaft 24, and ultimately the cutter 22 and its connected components, is desirable regardless of the mechanical connection allowing such movement. The movement allows the cutter 22 and, in some embodiments, the drive shaft 24 to be withdrawn proximally during placement of the catheter sheath, or tubular body 12, in the vasculature. Following positioning, the cutter 22 may then be advanced forward into a cutting position. Such a configuration allows increased maneuverability and flexibility during positioning and easier tracking through the vasculature. This configuration also allows for easier sterilization of the outer tubular body 12 in a compact coiled package. However, as will be recognized by those of skill in the art, such relative axial movement of the cutter 22 and the tubular body 12 is not necessary for utilization of various other aspects and advantages of the current invention.

A small drive plate 103, bonded to the rear end of the transfer shaft 107, advantageously couples with a drive sleeve 105 that is attached to the approximately 0.078 inch outside diameter motor shaft 92. The drive plate 103 may be any of a number of geometric configurations. Preferably, the drive plate 103 is a rotationally symmetrical shape having a central aperture although other configurations may also be used. The symmetry facilitates rotational balancing. In one embodiment, the drive plate 103 is square with a central aperture, triangular with a central aperture, or circular with a central aperture, with a connecting member to tie the drive plate to the drive sleeve with a reduced likelihood of slippage. Together, the drive plate 103 and the drive sleeve 105 form a concentric drive coupling, similar to a spline connection, between the motor shaft 92 and the transfer shaft 107.

The transfer shaft 107, in turn, may be connected to the flexible drive shaft 24. The concentric drive coupler configuration preferably allows approximately 0.25 inch of relative longitudinal movement between the drive plate 103 and the drive sleeve 105, which is sufficient to accommodate thermal and mechanical changes in the relative lengths of the outer tube 12 and flexible drive tube 24. An integral flange on the drive plate 103 or the drive sleeve 105 may serve as a shield to deflect fluid away from the rear motor bearings in the event of a leaking fluid seal. Thus, the drive sleeve 105 is preferably a solid walled annular flange which acts as a tubular deflection as will be understood by those of skill in the art.

The drive sleeve 105 and the drive plate 103 are preferably molded from Plexiglas-DR, a medical-grade, toughened acrylic resin made by Rohm and Haas. These parts have shown little tendency to crack in the presence of the chemicals that might be present or used in the assembly of the device; these chemicals include cyanoacrylate adhesives and accelerators, motor bearing lubricants, alcohol, epoxies, etc. The drive sleeve 105 and the drive plate 103 are also preferably lightly press-fitted to their respective shafts 92, 107, and secured with a fillet of adhesive applied to the outside of the joints.

With continued reference to FIG. 9, an infusion manifold 108 may be arranged at the proximal end of the control 18. The infusion manifold 108 is preferably designed as an input circuit; thus any fluid that can be pumped or injected at a pressure exceeding the diastolic pressure in the artery or vein could be used, but saline solutions, therapeutic drugs and fluoroscope contrast media are most likely to be used with this device. For instance, saline solutions may be used to purge air from the tubular body 12 and drive tube 24 before performing procedures such that air embolism may be avoided, and may also be used during an atherectomy procedure to provide a continuous flow of liquid (other than blood) during cutting to help carry debris through a return circuit. As will be recognized, the device 10 generally is purged of air prior to performing procedures. In such a case, an infusion pump or elevated IV bag may be used to ensure a continuous, low-pressure flow of saline solution through the system, depending upon the application and procedure.

At various times during a procedure, the clinician may request that a bolus of contrast medium be injected into the instrument 10 to enhance a fluoroscopic image of the artery or vein, either to position or to direct the guidewire 28, to locate a blockage, or to confirm that a stenosis has indeed been reduced. Contrast medium is a relatively dense material and high pressure (usually several atmospheres) is usually required to force the material quickly through the small, elongated lumen 26 of the drive tube 24. Such a medium may be infused using an infusion pump, for instance.

In the case of the illustrated surgical instrument 10, the infusion manifold 108 may be comprised of several components. The first component may be an infusion port that may contain a medical infusion valve 109, such as that supplied by Halkey-Roberts Corp. This silicone rubber check valve assembly 109 is preferably designed to be opened by insertion of a male Luer-taper (or lock) fitting. The valve 109 more preferably stays open as long as the taper fitting remains in place, but desirably closes immediately if it is withdrawn. This action provides simple access when needed, but provides the required backflow protection to minimize loss of blood through this route.

The infusion valve 109 is preferably permanently bonded into a side arm of a flush port manifold 111, an injection-molded, transparent acrylic fitting. The flush port manifold 111 desirably has an integral threaded extension that may protrude from the proximal side of the control 18. The threaded extension may be provided with a silicone guidewire seal 113, and an acetyl (Delrin) guidewire clamp nut 112 that together function as a hemostasis valve compression-fitting. Delrin may be used for the clamp nut 112 to minimize stiction and galling of the threads during use. Note that the materials indicated for the compression-fitting may be varied as will be recognized by those of skill in the art. An internal shoulder on the threaded portion of the nut 112 advantageously acts as a position stop, preventing extrusion of the seal 113 that might otherwise result from over-tightening. The guidewire 28 desirably extends through both the seal 113 and the nut 112.

When the clamp nut 112 is tightened, the guidewire seal 113 may compress against the guidewire 28 to lock it in place and to prevent leakage of blood or air through the seal 113. When it is necessary to slide the guidewire 28, or to slide the surgical instrument 10 along the guidewire 28, the clamp nut 112 is first loosened to reduce the clamping action somewhat and the relative movement is then initiated. If no guidewire 28 is used, the seal 113 may compress against itself and close off the passageways to reduce or prevent leakage.

A fluid channel advantageously extends through the flush port manifold 111, continuing through the open lumen of the drive tube 24, through a distal aperture 39 in the distal extremity of the cutter 22. The guidewire 28 preferably follows the same path. A leak-proof connection between the flush port manifold 111 and the drive tube 24 is therefore desirable.

Accordingly, a flush port flange 106 may be bonded to the motor end of the flush port manifold 111, creating a chamber housing a low durometer butyl rubber lip seal 114. The flange 106 may be manufactured of molded acrylic or the like. The lip seal 114 forms an effective dynamic seal against one end of the transfer shaft 107. Lip seals are pressure-compensating devices that function at zero or low pressure by light elastomeric compression against a shaft, minimizing the drag component in a dynamic application. When pressure against the seal increases, the lip tightens against the shaft, increasing both the sealing action and the dynamic friction. In this application, however, a high pressure sealing requirement preferably is only encountered during injection of contrast medium, typically when the cutter 22 is not rotating. Lower pressure dynamic sealing may be required during saline infusion, however, so pressure compensating lip seals are presently preferred.

The lip seal 114 is desirably transfer-molded butyl rubber, with about a 0.047 inch inside diameter lip (generally within the range of from about 0.035 inch to about 0.050 inch), running on the transfer shaft 107, which may have an outside diameter of approximately 0.055 inch. Medical-grade silicone grease may be used lubricate the interface between the lip seal 114 and the transfer shaft 107, but the grease tends to be forced away from the lip during prolonged use. Thus, a Teflon coating on the transfer shaft 107 may act as a back-up lubricant to reduce or eliminate seal damage in the event the grease is lost.

Returning to the vacuum manifold 86, as illustrated in FIG. 9, the vacuum hose 88 may be attached to the remaining port of the Y-shaped vacuum manifold 86. The hose 88 may be attached in any suitable manner as will be appreciated by those of ordinary skill in the art. The vacuum hose 88 generally extends between the vacuum manifold 86 of the control 18 and a vacuum source (see FIG. 1) such as a house vacuum of the catheter lab of a hospital or a vacuum bottle.

The vacuum hose 88 desirably extends through a switch configuration 120 described in detail below. In the illustrated embodiment, the vacuum hose 88 then further extends to the bottom portion of the control 18. A pinch resistant sleeve 116 may be provided to prevent the pinching of the vacuum hose 88 as it exits the control 18. Additionally, the pinch resistant sleeve 116 provides a liquid seal to further reduce the likelihood of liquids entering the control 18 unit during operation.

In interventions such as those with which the present surgical instrument 10 has particular utility, it has been discovered to be desirable that cutting should occur only under sufficient aspiration. Accordingly, an aspect of the present invention involves a cutter lock-out mechanism that will not allow cutting of material unless sufficient aspiration is present. The aspiration rate may be directly sensed (i.e., flow monitoring) or indirectly sensed (i.e., vacuum monitoring). For instance, because the level of vacuum will typically be one determining factor of the level of aspiration, the vacuum level may be monitored to determine when a new vacuum bottle should be employed. In such a situation, if the level of a sensed vacuum drops below about 15 inches Hg, insufficient clearing vacuum is present and the risk of blockage within the device 10 increases. Thus, a cutter lock-out mechanism should be employed to prevent cutting of material until the vacuum level is replenished. Specifically, it has been determined that a sensed vacuum of about 13.5 to about 14 inches Hg usually precedes clogging in the illustrated embodiment.

The cutter lock-out mechanism is generally comprised of two components, either of which may find utility individually or in combination. One of the components is a vacuum monitor. The vacuum monitor (not shown) is desirably a linear pressure transducer that senses the presence of an adequate vacuum force. The signal from the transducer is preferably utilized to enable an automatic override of the motor such that the motor cannot turn the cutter 22 if the vacuum drops below a threshold level (e.g. 15 inches Hg). Generally, the vacuum monitor may also comprise a vacuum detector, a comparator of any suitable type, an alarm or circuit cut-out. Thus, the vacuum detector may sample the state of operation of the vacuum, the comparator may determine varying operating conditions, and if the vacuum force drops below or unexpectedly and suddenly exceeds the pre-set threshold level for any reason the alarm can alert the operator to take corrective action, and/or the cut-out circuit can automatically stop rotation of the cutter.

The cutter lock-out mechanism may also comprise a flow monitor (not shown). The flow monitor may be of any suitable type and may simply monitor the flow rate, or aspiration rate, through the aspiration channel. The flow monitor also may be connected to circuitry or alarms such that the user may be warned if the aspiration rate slows (i.e., conditions indicative of a blockage arise) and/or such that the device 10 may automatically take corrective action when a decrease in the aspiration rate is detected. For instance, the device 10 may disable cutting (i.e., rotation of the cutter 22), increase the suction level or otherwise attempt to auto-correct the situation. Also, it is anticipated that various alarms, be they visual, tactile or auditory, may be utilized to inform the operator or clinician of the alert status.

Another component of the cutter lock-out mechanism is a switch arrangement that advantageously controls the motor state and vacuum application as described below. As will be recognized by those of skill in the art, such a switch may be mechanical, electromechanical, or software-controlled. With reference to FIGS. 9A-9C, a schematically illustrated switch configuration 120 desirably assures that the motor 90 driving the rotatable drive shaft 24, which in turn drives the cutter 22, may not be activated unless the vacuum is being applied. The illustrated pinch valve switch 120 generally comprises a push button oriented along the Z axis shown in FIG. 10A. The switch push button 124 may translate along the Z axis when depressed by the user. Desirably, the lower portion of the push button 124 is provided with a u-shaped cut out forming a tunnel along the x-axis. The cut out is preferably sized to correspond to a compression spring 126 extending therethrough. The presently preferred compression spring 126 is a precision-length stack-wound button spring fabricated from 0.027" diameter 302 stainless steel wire, with a closed retainer loop at one end. The push button 124 may be positioned along a portion of the compression spring 126 such that the push button 124 rests on the compression spring 126 and is supported in an up position. The switch push button 124 thus can travel to a down position when depressed by the operator to a position such as that shown in FIG. 10B. The compression spring 126 provides a bias such that the push button 124 will return to the up position when released. Of course, any other suitable biasing mechanism or component may also be used.

The switch push button 124 may be further provided with an axial arm 128 that preferably extends in a direction perpendicular to the direction of travel of the push button 124. Thus, in some embodiments, the arm may assume an "L" shaped configuration. It is anticipated that a variety of arm configurations may also be employed.

An electronic switch 130 is desirably located below the axial arm 128 of the switch push button 124. Thus, as the push button 124 is further depressed beyond the position in FIG. 10B, to a position such as that illustrated in FIG. 10C, contact is made on the electrical switch 130. The electrical switch 130, when closed, allows current to flow from a power source 122 to the motor 90. Thus, depression of the push button 124 creates a flow of current that drives the motor 90. The motor 90 drives the drive tube 24 and cutter 22 of the present surgical instrument 10 as described above.

Advantageously, the compression spring 126 is also preferably attached to a pinching member 132 of the switch configuration 120. As the push button 124 is depressed, the compression spring 126 is advantageously initially deflected. Desirably, the deflection in the compression spring 126 causes the pinch member 132 to retract. Thus, the pinch member 132 is retracted once the push button 124 is depressed. As the pinch member 132 is retracted, a vacuum is initiated and aspiration flow is allowed to pass the pinch valve 120. Advantageously, the amount of flow past valve may depend on how far the button 124 is depressed, enabling control of the amount of suction (and, thereby, the level of aspiration) if desired. Further depression of the push button 124 beyond the retraction point initiates a contact of the electrical switch 130 and, therefore, allows the motor 90 to be powered only after the vacuum flow has begun.

Figure 10A:
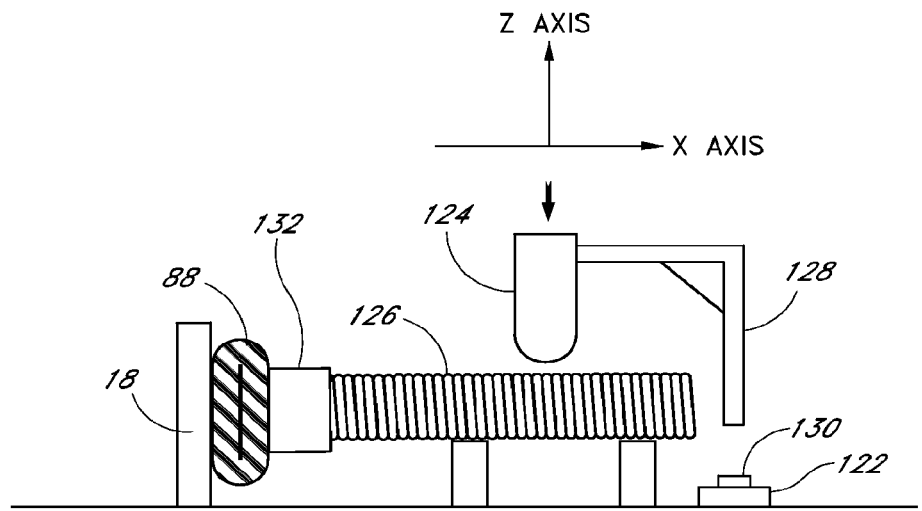
FIG. 10A is a schematic illustration of a pinch-valve switch in a position which interrupts an applied vacuum and interrupts power flow to a drive motor.
Figure 10B:
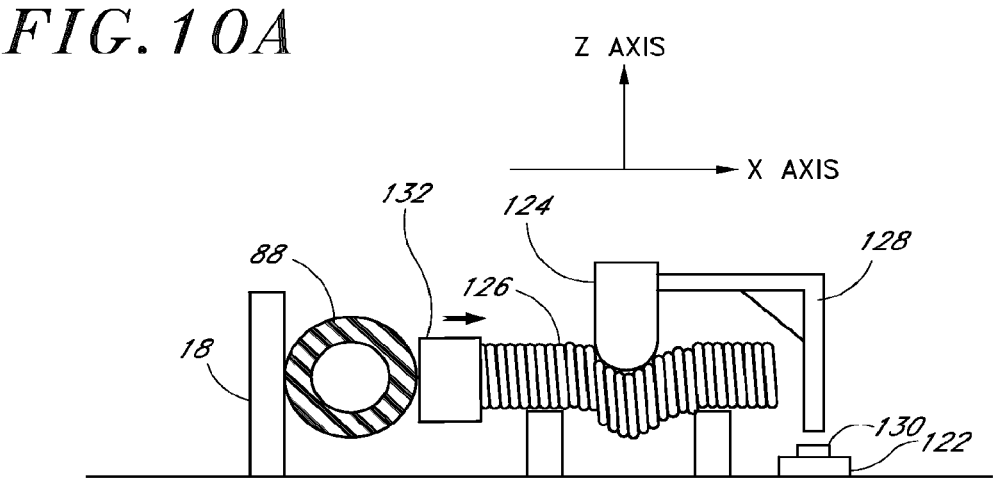
FIG. 10B is a schematic illustration of a pinch-valve switch in a position that applies the vacuum and interrupts power flow to the drive motor.
Figure 10C:
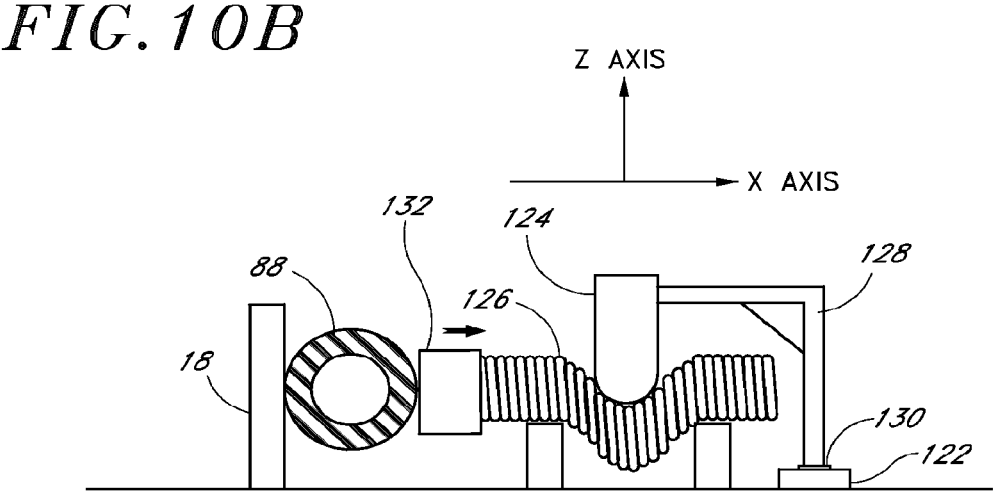
FIG. 10C is a schematic illustration of a pinch-valve switch in a position which applies the vacuum and allows power to flow to the drive motor.

FIG. 10A illustrates a relaxed, non-depressed condition in which the vacuum hose 88 is closed by the pinch valve 132 and the spring 126, and the electrical switch 130 which controls power supply to the motor 90 is open. With reference to FIG. 10B, the push button 124 is partially depressed, thereby causing the vacuum hose 88 to be opened while maintaining the electrical switch 130 open. Further depression of the push button 124, illustrated in FIG. 10C, closes the electrical switch 130 while the vacuum hose 88 is maintained in an open state. Thus, depressing the push button 124 an initial amount starts the vacuum first and further depression initiates the cutting action. Such timing reduces risks associated with cutting without aspiration. Because repeated cycles of opening and closing the valve may tend to shift the position of the tube 88, internal ribs (not shown) are preferably provided in the control 18 to maintain the proper position of the tube 88.

A return flow path of the illustrated device 10 for aspiration and the like starts at the cutter 22, passes through the helical thread 46 and the cutter blocks 42 of the cutter 22 (and stationary blocks of the cutter housing, if present), continues through the outer lumen 20 of the outer tube 12 to the vacuum manifold 86, and then passes through a length of vacuum tubing 88 to a tissue collection/fluid separation container, such as a vacuum bottle. The return flow may be assisted by a positive vacuum supply, such as the vacuum bottle or a house vacuum, as is known in the art. For instance, the collection container may be connected to a vacuum collection canister that may be, in turn, hooked to a regulated central vacuum source or a suction collection pump or evacuated container.

The pinch valve assembly is preferably designed with a "shipping lock-out" feature (not shown) that secures the button 124 in a partially depressed position where the vacuum tube 88 is no longer compressed, but the switch 130 is not yet actuated. This preserves the elastic memory of the pinch tube and protects the device from accidental actuation during handling or storage. In its present form, a thin, flexible lock-out wire with an identifying tag (not shown) can be inserted at the last stage of instrument manufacturing, passing through a hole in the button (not shown) and extending through a notch in the side wall of the control 18. In this configuration, a highly-visible tag protrudes from the side of the control 18, preventing use of the device until the wire is pulled free. Removing the lock-out wire releases the button 124 and returns the control 18 to a functional condition. Once removed from the original locked position, the lock-out wire (not shown) desirably cannot be reinserted without disassembly of the control 18.

Figure 11A:
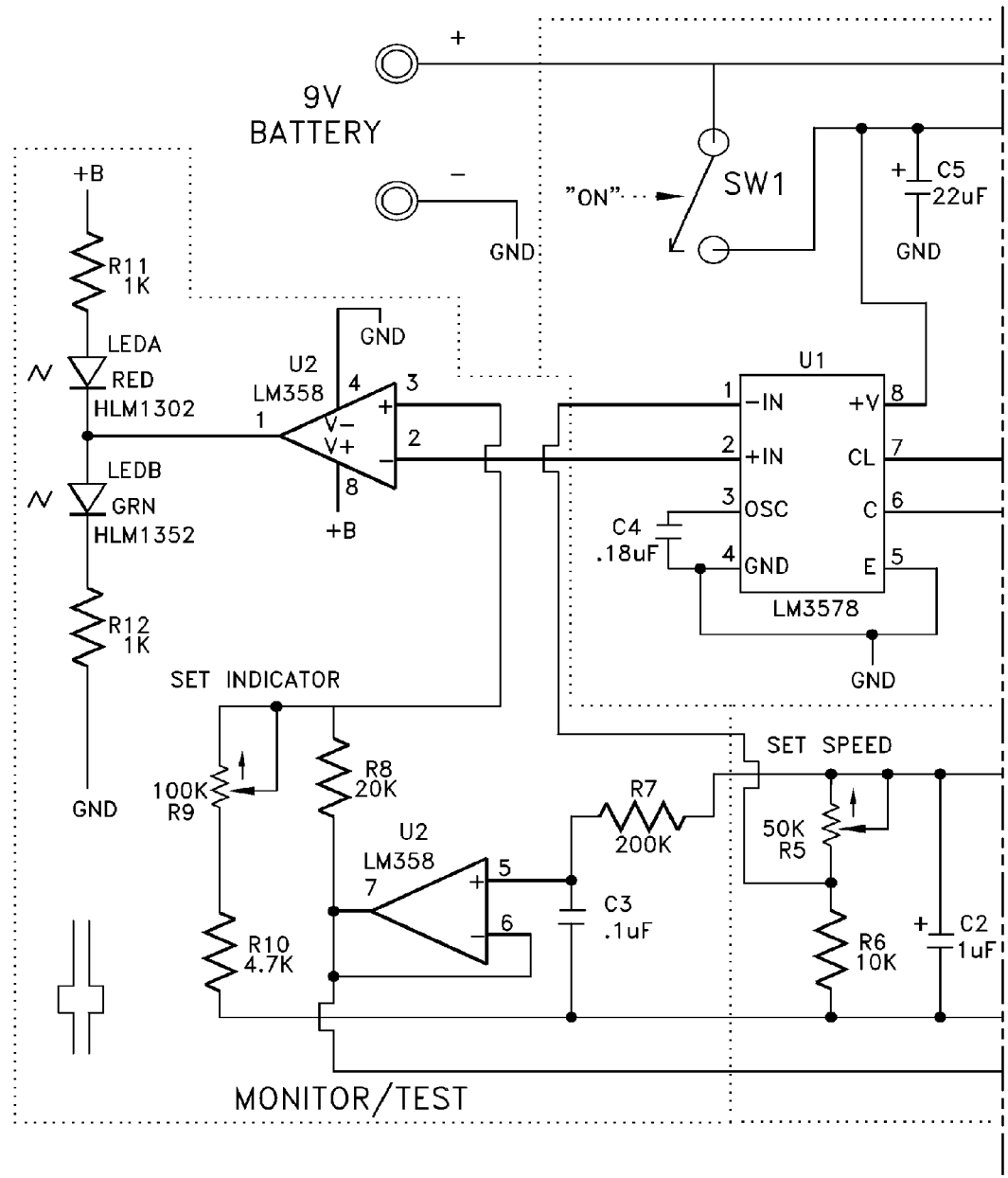
FIG. 11A is a schematic illustration of the left portion of a representative motor control circuit in accordance with the present invention.
Figure 11:
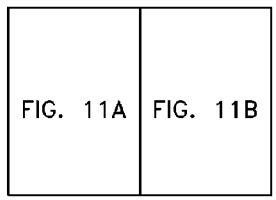
FIG. 11 is a schematic illustration of a representative motor control circuit in accordance with the present invention.
Figure 11B:
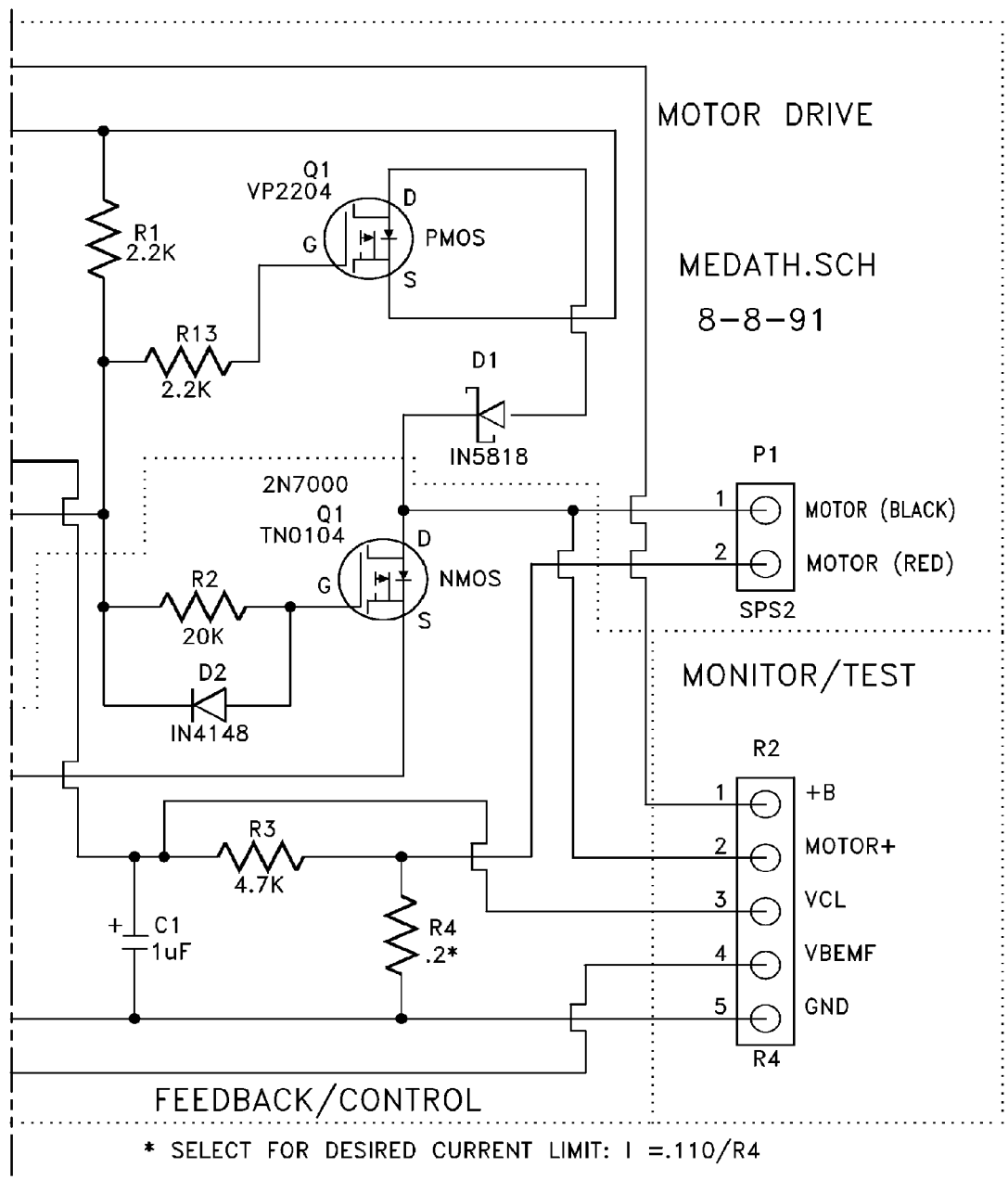
FIG. 11B is a schematic illustration of the right portion of a representative motor control circuit in accordance with the present invention.

With reference again to FIG. 9, the device 10 is preferably controlled by electronic circuitry such as may be contained on a printed circuit board 133. The circuitry providing the power to the motor 90 may also include a circuit to check the load on the motor. An exemplary motor control and feedback circuit is illustrated in FIG. 11; FIG. 11A illustrates the left portion of this representative motor control circuit, and FIG. 11B illustrates the right portion. However, as will be readily recognized by those of ordinary skill in the art, many other motor control circuits may also be implemented. As is known, when a direct current motor, as used in this invention, encounters resistance to rotational movement, an increased load is placed on the power source 122. Accordingly, as described below, the circuitry is provided with the capability to identify, indicate, record and possibly compare the speed and/or torque to previously recorded speeds or torques. Specifically, the speed and/or torque, as indicated by the level of current to the motor, may be compared over time through the use of a comparator. Additionally, a reverse switch may be provided to reverse out of jams or potential jams when necessary. Such a reverse switch may be a momentary switch or any other suitable switch as will be recognized by those of skill in the art.

As described below in detail, a motor controller 134 preferably provides the motor 90 with sufficient energy by using a combination of missing pulse and pulse width modulation. For instance, the motor speed may be sensed by measuring the back electromotive force (EMF), which is proportional to speed. A portion of the back EMF may be fed to the controller 134, which preferably varies the drive power to the motor 90 to maintain a constant speed. The circuit values of the controller 134 allow motor speed settings of about 1,000 RPM to about 8,000 RPM. The speed chosen for no load operation in one embodiment may preferably range from approximately 1,500 RPM to about 5,000 RPM. In a presently preferred embodiment, the no load operation speed is approximately 2,000 RPM. Desirably, the motor speeds associated with the present invention are less than those associated with abrasive-type devices and turbulence-based devices as will be recognized by those of skill in the art. In some embodiments, the motor control circuitry may limit the motor torque to a range of about 0.10 oz-inches to about 0.45 oz-inches by sensing the motor current and setting the motor drive power to the appropriate level. A switching controller, thus, may be used for two reasons: (a) it is very efficient—it uses less than 0.015 amperes (the motor current would vary from 0.05 to 0.4 amperes, or perhaps more), and (b) it can deliver appropriate torque instantly or on demand, even at low motor speeds, so the likelihood of stalling is minimized.

The power source 122, preferably a 9-volt battery, may not be electrically connected to the controller 134 until the push button 124 is depressed, as discussed above, so standby power drain is advantageously eliminated or reduced. In the illustrated embodiment, a light emitting diode (LED) is desirably on when the motor is running at normal loads (i.e., the sensed current level is lower than a predetermined current level requiring an alert). This LED may be green in some embodiments and will be referred to as such in connection with the illustrated embodiment. Another LED turns on at a motor current of approximately 0.25 amperes, or another threshold level that may indicate a motor "overload" situation. This LED may be red in some embodiments and will be referred to as such in connection with the illustrated embodiment. For instance, the red LED may indicate that the current is proximate, or has achieved, a predetermined maximum safe value. The preset maximum safe value is the upper limit, as determined by the specific design and configuration of the device 10, for current that indicates an overload condition. Thus, another feature of the present invention includes the ability to provide feedback to the operator based upon motor load. This is advantageous in that the operator can be alerted to a potential binding of the instrument and react accordingly. For instance, the progression rate of the instrument may be reduced or stopped or the instrument may be backed from the trouble location using the reverse switch or otherwise. It should also be understood that the device may make automatic adjustments to the motor speed relative to the sensed load utilizing methods which would be readily apparent to one skilled in the art following a review of FIG. 11.

Any of a variety of tactile, auditory or visual alarms may also be provided either in combination with, or as alternatives to, each other and the LEDs. For instance, the surgical instrument could vibrate or provide an audible signal when it encounters an overload situation. The pulses or tones may vary to correspond to any variance in resistance to rotation. For example, the pitch may increase with resistance or the speed of a repeating pulse of sound may increase. Additionally, where a (CRT) monitor is used to visualize the operation, a visual signal could be sent to the monitor to display the operating characteristics of the surgical equipment. As will be further recognized to those skilled in the art, other variations of alerting the operator to the operating characteristics of the present invention may be provided.

The present invention thus provides feedback to the clinician in real time during the progress of the rotational atherectomy procedure. Real time feedback can allow the clinician to adjust the procedure in response to circumstances that may vary from procedure to procedure, thereby enhancing the overall efficiency of the procedure and possibly minimizing additional risks such as the creation of emboli. Pressing the cutter 22 into a lesion with too much force may produce an increased load, which can then be detected by the circuitry 131 and communicated to the clinician in any of a variety of ways as has been discussed. This may allow the clinician to ease back on the distal advancement force and/or adjust the vacuum or RPM of the cutter 22, such as by reducing the advancement force and lowering the resistance to rotation of the cutter 22, until the load is reduced to an acceptable level, and continue with the procedure. As will be recognized, if aspiration drops due to increased material being aspirated, the load is likely to have increased; therefore, the clinician is alerted to such an increase in load such that corrective action may be taken. By allowing the load to return to an acceptable level, the aspiration rate may also return to an acceptable level in some embodiments. As will be recognized, the load may increase due to a blockage and the blockage would lower the aspiration rate; however, clearing the blockage will generally return the aspiration rate to a desired level as well as reduce the load on the motor.

In addition, increased load can be incurred by kinks at any location along the length of the instrument, thereby reducing the motor speed. Kink-originated loading could be reflected in the feedback mechanism to the clinician, so that the clinician can assess what corrective action to take.

Another aspect of the present invention involves a selectively reversible tip rotation. For instance, the drive motor may be reversed such as by manipulation of the reverse control switch (not shown) on the handle of the control 18. Motor reversing circuitry, with or without a variable speed control, is well understood by those of skill in the art. Momentary reversing of the direction of rotation of the distal cutter, most likely at a relatively low speed of rotation, may be desirable to dislodge material which may have become jammed in the cutter tip. In this manner, the clinician may be able to clear a cutter tip blockage without needing to remove the catheter from the patient and incur the additional time and effort of clearing the tip and replacing the device. Low speed reverse rotation of the cutter may be accomplished in combination with a relatively increased vacuum, to reduce the likelihood of dislodging emboli into the blood stream. Following a brief period of reverse rotation, forward rotation of the cutter tip can be resumed. Whether the obstruction has been successfully dislodged from the cutter tip will be apparent to the clinician through the feedback mechanisms discussed above. Moreover, it is anticipated that the device may alternatively have substantially the same torque, speed, vacuum force, and alarm thresholds when the cutter is rotated in either direction. It is, however, presently preferred to utilize the same speed of rotation in both forward and reverse rotation.

In the presently preferred embodiment of the control and power supply circuitry illustrated in FIG. 11, the motor controller has an LM3578A switching regulator, indicated generally by U1 in FIG. 11. The switching regulator may be an LM3578A switching regulator in some embodiments; one of ordinary skill in the art will readily recognize other components and circuitry that can perform essentially the same functions. The switching regulator is normally used as a power supply regulator, wherein it may provide a substantially constant voltage regardless of load. A negative in jack (pin 1) may be used as an error input. For instance, when the voltage at pin 1 is less than about 1 volt, an inference may be established that the motor speed may be too low, therefore the output jack (pin 6) goes low. When the output at pin 6 goes low, it may cause a gate (pin G) of Q1 to be near 0 volts. As will be recognized, this may cause Q1 to turn on with a resistance of about 1.3 ohms in the illustrated embodiment. Advantageously, the end result is that the motor, Q1, D1 and R4 may be connected in series across the battery. The motor current will likely be rather heavy, so the motor speed may increase. This "on" condition lasts for a time that is preferably controlled by U1's oscillator, whose frequency (about 500 Hz) may be set by C4. Also, the switching regulator U1 desirably limits the output on time to about 90% of this 2-millisecond period (1/frequency=period) because it uses the first 10% portion purely for comparing the error signal to the reference. The comparison advantageously continues during the 90% period, with the output on or off as determined by the error signal. If the motor speed were to increase to the proper level during the 90% portion of the cycle, the output would preferably shut off immediately, thereby resulting in a narrowed pulse. Hence, pulse width modulation is achieved.

Desirably, the output of the switching regulator U1 only goes low, so R1 preferably pulls the output high when the switching regulator U1 is off. R13 isolates the switching regulator U1 from the gate capacitance of Q1, thereby advantageously ensuring a more reliable start-up of the switching regulator U1 upon application of power. D1 preferably prevents below-ground motor switching transients from reaching the transistor Q1. In the illustrated embodiment, the VP2204 may have a 40-volt rating, which advantageously provides plenty of margin for withstanding voltage transients. As will be recognized by those of skill in the art, any other suitable control circuit may also be utilized. Power supply filter C5 preferably helps provide the large short duration currents demanded by the controller, especially when the battery power is nearly depleted.

In the illustrated embodiment, an N-channel FET, indicated by reference numerals Q2, preferably switches the motor's back EMF to a storage capacitor C2 during the portion of the control cycle when the motor is not powered (i.e., Q2 is off when Q1 is on, and vice versa). The resistor R2, along with the gate capacitance of the FET Q2, advantageously forms a delay network so that when the FET Q2 turns on after the FET Q1 turns off. This configuration may block turn-off transients and may present a voltage to C2 that more accurately reflects the back EMF. The FET's Q2 turn-off need not be delayed, so D2 may turn on with negative-going signals and may parallel the resistor R2 with a low impedance, thereby giving only a slight delay. A resistor R5 and a resistor R6 preferably divide the back EMF to provide the error voltage (nominally about 1 volt) to pin 1 of the switching regulator U1. The value of the resistor R5 desirably determines the level of back EMF, and, therefore, the motor speed required to produce about 1 volt at the switching regulator U1, pin 1.

The resistor R4 may be in series with the motor and may be used to sense the motor current and limit the motor torque accordingly. For instance, the current pulses through the resistor R4 generate voltage pulses, which may be integrated (averaged) by the resistor R3 and the capacitor C1 and fed to pin 7 of the switching regulator U1, which is the current limit input. Preferably, when the voltage at this pin is about 0.110 volts or more, the switching regulator U1 may not increase the output drive, regardless of the error voltage. The circuit values shown result in about 0.45 amp average, or between about 0.45 and about 0.5 oz-in. of stall torque for the motor.

The back EMF voltage stored by the capacitor C2 is preferably further filtered by a resistor R7 and a capacitor C3 and may appear at the output (pin 7) of an amplifier (U2) as a relatively noise-free signal which follows the motor speed with a slight time lag. The amplifier in the illustrated embodiment is an LM358 buffer amplifier. The voltage is desirably divided by a resistor R8, a resistor R9 and a resistor R10 and may appear at the positive input of the comparator section of the amplifier U2 (pin 3). A negative input is desirably fixed at about 1 volt, since it is connected to the switching regulator U1, pin 2. When the voltage at pin 3 exceeds that at pin 2, the output (pin 1) is high and the green (Cutting) LED is on in the illustrated embodiment. When the voltage at pin 3 is less than at pin 2, the output is low and the red (Overload) LED is on in the illustrated embodiment. "Overload" in the embodiment being described herein has been defined as the point when the motor current reaches about 70% of stall current; however, any desired percentage of stall current may be used to define an overload condition. The value of a resistor R9 determines approximately equal red and green LED intensities with a dynamic motor load that causes a motor current of approximately 0.35 amperes.

With continued reference to FIG. 11, a test connector P2 provides signals and voltages for production testing of the controller board, which may be tested as a subassembly prior to installation. The test connector P2 may also be accessible when the top half of the housing is removed, such as for testing at higher levels of assembly. It should be appreciated that one of skill in the art may modify the test connector and related circuitry such that the connector could also become a data bus all data to be passed from the control to a recorder, a display or the like.

In a presently preferred method of use, a guidewire 28 is first percutaneously introduced and transluminally advanced in accordance with well known techniques to the obstruction to be cleared. The surgical instrument 10 is then introduced by placing the distal end 16 of the flexible tubular body 12 on the guidewire 28, and advancing the flexible tubular body 12 along the guidewire 28 through the vessel to the treatment site. When the distal end 16 of the flexible tubular body 12 has been maneuvered into the correct position adjacent the proximal terminus of material to be removed, the drive tube 24 is rotated relative to the tubular body 12 to cause the cutter 22 to rotate in a direction which will cause the forward end 47 of the thread 46 to draw material into the housing 21. A circular cutting action may be provided by mutual cooperation of the outer cutting edge of the screw thread 46 with lip 39 of the cutter housing 21 and the internal peripheral wall of the cutter housing 21. In addition, the cutter housing 21 in cooperation with the flanges 42 and any other stationary members present, effectively chops or minces the strands of material being drawn into the cutter housing 21. The cut material is then carried proximally through the annular passageway between the flexible drive tube 24 and the tubular body 12 under the force of vacuum. If an increase in load and/or decrease in RPM is detected, the clinician can take reactive measures as described above. The vacuum preferably pulls the cuttings through the entire length of the lumen 20 and vacuum tube 88 and into a suitable disposal receptacle. A manual or automatic regulator may regulate the vacuum source such that a constant flow velocity may be maintained, or blockages reduced or cleared, through the vacuum tube 88 regardless of the viscosity of the material passing through the vacuum tube 88.

Figure 12:
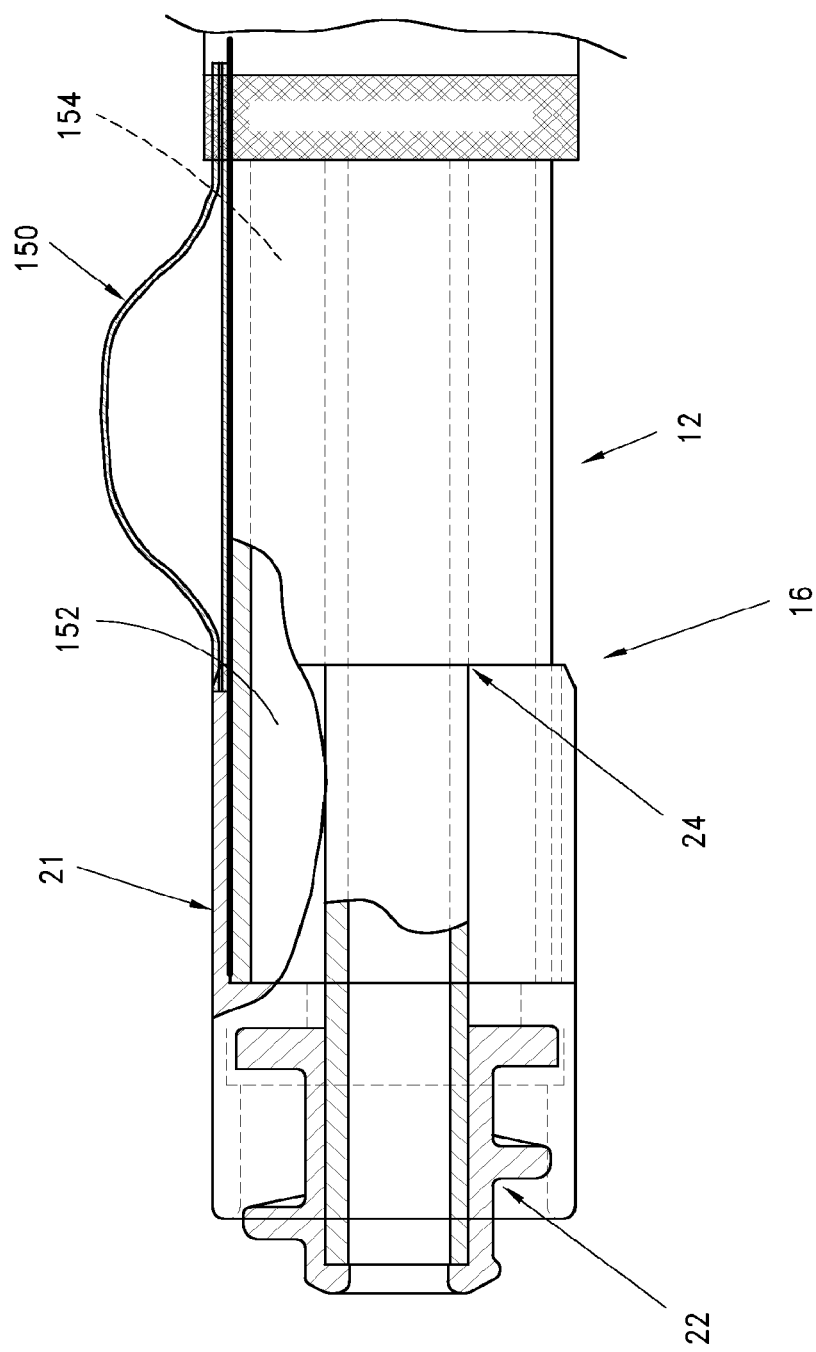
FIG. 12 is an enlarged, partially sectioned side view of a cutter, housing and catheter assembly configured in accordance with certain aspects and advantages of the present invention.

With reference now to FIG. 12, a further aspect of the present rotational atherectomy device will be described in detail. As illustrated, the elongate flexible member 12 preferably includes an expandable component 150 near the distal end 16 of the flexible member 12. More preferably, the expandable component 150 is positioned proximate the cutter housing 21 at a location directly adjacent the proximate end of the housing 21. In some embodiments, the expandable member 150 may be positioned on the housing 21 itself.

The expandable member 150 preferably extends about only a portion of the total circumference of the flexible member 12. In this regard, the expandable member is used to offset the cutter tip 22 such that the axis of rotation of the cutter tip is disposed about a second axis that is generally parallel to an axis of the artery in which the device is disposed but the cutter tip axis is laterally displaced from the axis of the artery. Specifically, as the expandable member 150 is inflated, or expanded, the expandable member 150 contacts one of the sides of the artery, thereby displacing the flexible member 12 and the cutter tip 22 in a radial direction away from the center of the artery. In the illustrated embodiment, the expandable member 150 extends about 75☐ around the circumference of the flexible member 12. In other embodiments, the expandable member may extend around between about 45☐ to about 270☐.

The expandable member may comprise any of a number of components. For instance, the illustrated expandable member is a Pellethane balloon having eccentric tails 152. The presently preferred material, Pellethane, forms a compliant balloon that allows the diameter to grow with increases in inflation pressure. The preferred variant of Pellethane is 2363-90AE which allows a working pressure of between about 10 psi and about 60 psi with diameter growths of between about 1.5 mm to about 2.0 mm. Of course, other materials may be chosen depending upon the application. In other embodiments, the working pressure may range from about 5 psi and about 50 psi with diameter growths of between about 0.8 mm and about 3.0 mm. The inflatable portion of the balloon preferably has an axial length of between about 8 mm and 2 mm with a more preferred length being about 5 mm. In arrangements having an inflatable length of about 5 mm, it is anticipated that about 3 mm of the balloon will be useful in offsetting the cutter tip 22 relative to an axis of the lumen in which the cutter tip 22 is disposed.

The eccentric tails 152 of the balloon also form a part of the presently preferred arrangement. The eccentric tails 152 generally lie flat along the flexible member 12 to which they are attached. Such an arrangement allows the deflated profile of the device 10 to be decreased as well as eases the bonding between the expandable member 150 and the flexible member 12. While concentric tailed balloons may adequately function as the expandable member 150, the eccentric tailed balloons are presently preferred. The tails are preferably adhered to the flexible member with an epoxy resin or ultraviolet adhesive. In some arrangements, the tails 152 are preferably captured by external rings, housings or tubes.

An inflation lumen 154 extends between the expandable member 150 and a portion of the device 10 which is external to a patient. The lumen 154 may be formed within the flexible member 12 or may be positioned to the outside of the flexible member 12. The positioning of the inflation lumen 154 may be selected as a result of the application in which the device 10 will be used.

In use, the device 10 featuring the balloon operates in a similar manner to the device 10 described above. Specifically, as described above, the guidewire 28 is first percutaneously introduced and transluminally advanced in accordance with well known techniques to the obstruction to be cleared. The surgical instrument 10 is then introduced by placing the distal end 16 of the flexible tubular body 12 on the guidewire 28, and advancing the flexible tubular body 12 along the guidewire 28 through the vessel to the treatment site. When the distal end 16 of the flexible tubular body 12 has been maneuvered into the correct position adjacent the proximal terminus of material to be removed, the expandable element is inflated with a fluid in a known manner. The expandable member 150 acts as a deflecting mechanism to offset the cutter tip 22 from the centerline of the artery.

Figure 13:
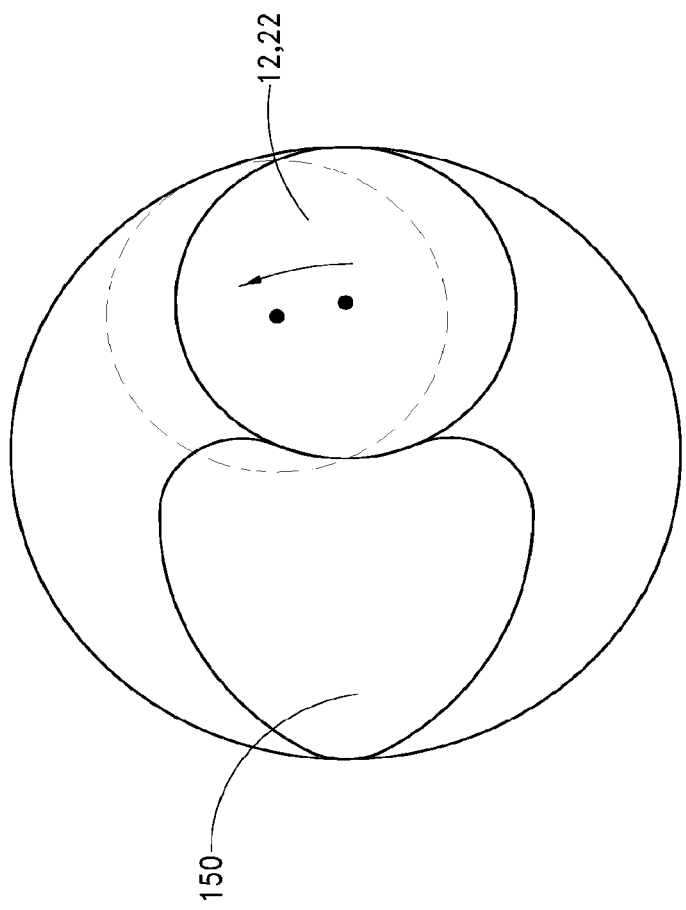
FIG. 13 is a schematic view of a treatment process performed according to a first mode of off-set operation.

At this point, any of at least two modes of operation may be used. In a first mode, illustrated schematically in FIG. 13, the drive tube 24 is rotated relative to the tubular body 12 to cause the cutter 22 to rotate in a direction which will cause the forward end 47 of the thread 46 to draw material into the housing 21. Also, suction may be used to pull material into the housing 21. A circular cutting action may be provided by mutual cooperation of the outer cutting edge of the screw thread 46 with lip 39 of the cutter housing 21 and the internal peripheral wall of the cutter housing 21. In addition, the cutter housing 21 in cooperation with the flanges 42 and any other stationary members present, effectively chops or minces the strands of material being drawn into the cutter housing 21.

The cutter tip 22 is then rotated in an eccentric rotation by turning the flexible member 12 while the cutter tip 22 is spinning in the housing 22. In one arrangement, the cutter tip is eccentrically rotated through a pass of about 360□; however, the sweep of the cutter tip may be varied depending upon any one of a number of factors. Also, the rotation of the flexible member 12 may be performed manually. After a complete rotation of the flexible member 12, the cutter tip 12 is then advanced forward through another portion of the material to be removed. The cut material is carried proximally through the annular passageway between the flexible drive tube 24 and the tubular body 12 under the force of vacuum. If an increase in load and/or decrease in RPM is detected, the clinician can take reactive measures as described above. The vacuum preferably pulls the cuttings through the entire length of the lumen 20 and vacuum tube 88 and into a suitable disposal receptacle. A manual or automatic regulator may regulate the vacuum source such that a constant flow velocity may be maintained, or blockages reduced or cleared, through the vacuum tube 88 regardless of the viscosity of the material passing through the vacuum tube 88.

Figure 14:
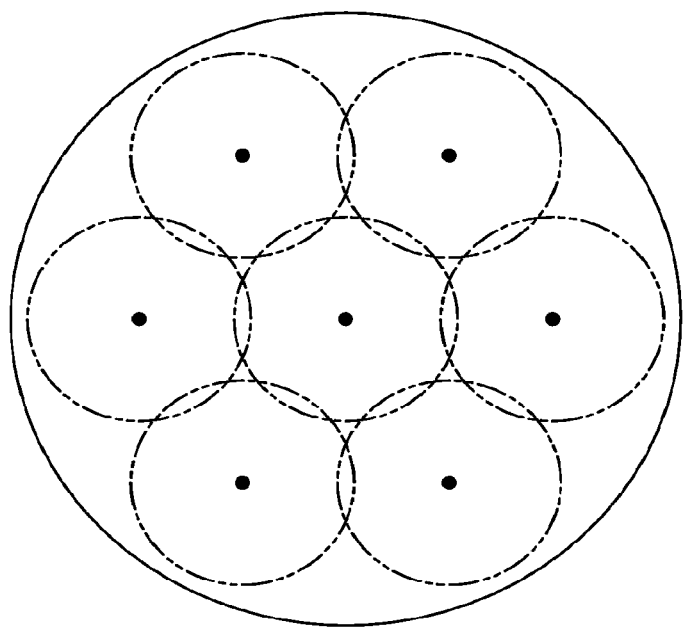
FIG. 14 is a schematic view of a treatment process performed according to a second mode of off-set operation.

In another mode of operation, illustrated schematically in FIG. 14, the cutter tip 22 is axially advanced through the material to be removed after the deflecting expandable member 150 is inflated. A circular cutting action may be provided by mutual cooperation of the outer cutting edge of the screw thread 46 with lip 39 of the cutter housing 21 and the internal peripheral wall of the cutter housing 21. In addition, the cutter housing 21 in cooperation with the flanges 42 and any other stationary members present, effectively chops or minces the strands of material being drawn into the cutter housing 21. The cut material is carried proximally through the annular passageway between the flexible drive tube 24 and the tubular body 12 under the force of vacuum. If an increase in load and/or decrease in RPM is detected, the clinician can take reactive measures as described above. The vacuum preferably pulls the cuttings through the entire length of the lumen 20 and vacuum tube 88 and into a suitable disposal receptacle. A manual or automatic regulator may regulate the vacuum source such that a constant flow velocity may be maintained, or blockages reduced or cleared, through the vacuum tube 88 regardless of the viscosity of the material passing through the vacuum tube 88.

After the cutter tip 22 has traversed the length of the material to be removed, the cutter tip 22 is withdrawn through substantially the same path of axial travel through the material. The expandable member 150 is then deflated and the flexible member 12 is reoriented for a second pass through the material. In some arrangements, the expandable member 150 may remain inflated or may be partially deflated during reorientation. The flexible member 12 may be rotated to any degree desired by the operator. In one arrangement, the flexible member 12 is rotated about 60 degrees from the first pass. This arrangement is illustrated schematically in FIG. 14. The expandable member 150 is then inflated and the cutter tip 22 is again axially advanced through the material to be removed. This process is repeated as desired in any particular application. In the illustrated arrangement, a non-offset pass is also performed such that the cutter tip 22 passes through a generally central location. One of ordinary skill in the art will readily recognize that the degree of overlap between passes may vary from operator to operator. Also, in instances in which the overlap is not extensive, the paths formed by the individual passes may coalesce into a single lumen.

As will be recognized, either of the above described modes of operation will result in an enlarged effective flow path as compared to the outside diameter of the device. It should be recognized that any combination of the modes of use of the deflection expandable member discussed directly above may also be used. The off-center cutting arrangement advantageously implements the device 10 in an operation which enlarges the diameter of the cleared material over and above the outside diameter of the catheter being used to house the cutter.

Figure 15A:
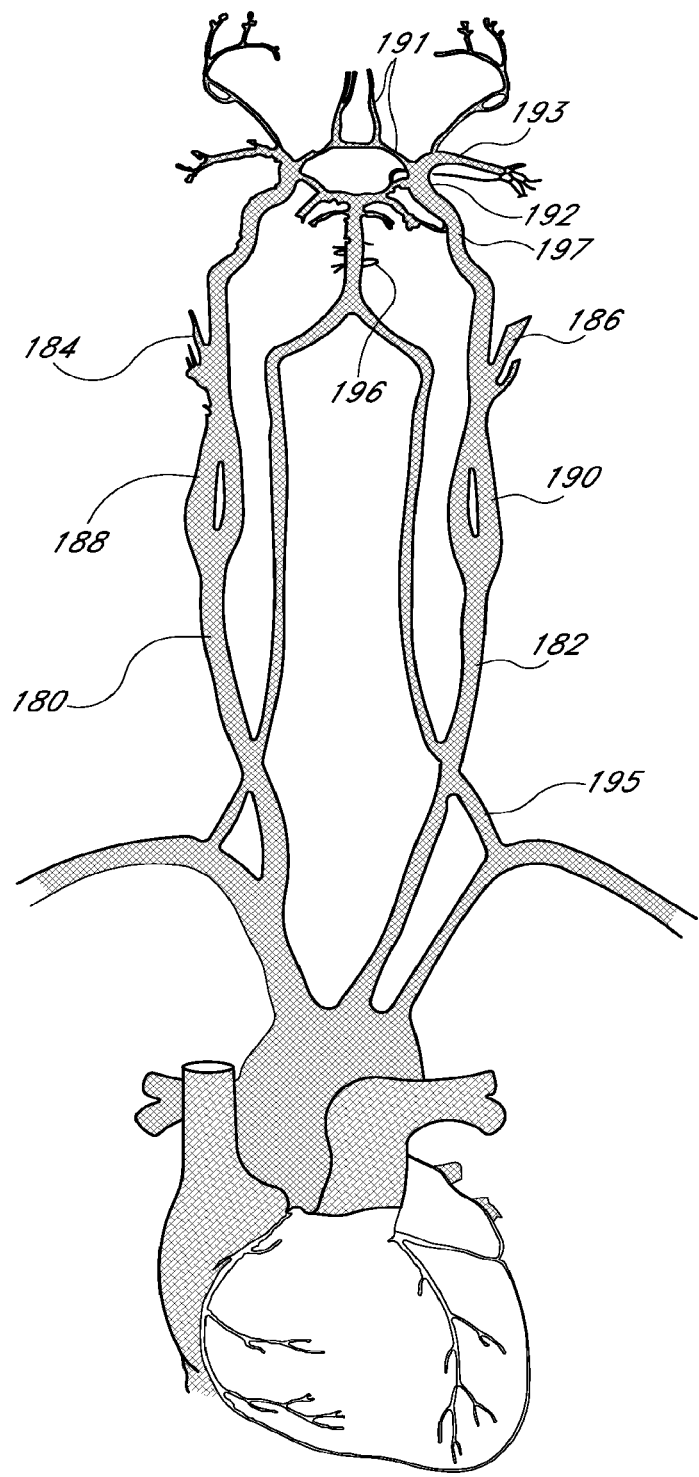
FIG. 15A is a schematic view of the middle cerebral artery anatomy and proximal arterial vasculature.

Referring to FIG. 15A, perfusion in the brain is achieved in part through the anterior cerebral circulation. The anterior circulation comprises the right and left common carotid arteries 180, 182, each of which branch into an external carotid artery 184, 186 and an internal carotid artery 188, 190. Due to the bilateral symmetry in the normal vasculature, only the left hemisphere will be detailed below. The left posterior communicating artery 192 branches off from the left internal carotid artery 190 near its terminus. The left internal carotid artery 190 then terminates in two branches: the left anterior cerebral artery 191 and the left middle cerebral artery 193. Also shown is the posterior circulation of the brain, which comprises the right vertebral artery and left vertebral artery 195, which converge to form the basilar artery 196 and its terminal branches, the right and left posterior cerebral arteries 197.

Figure 15B:
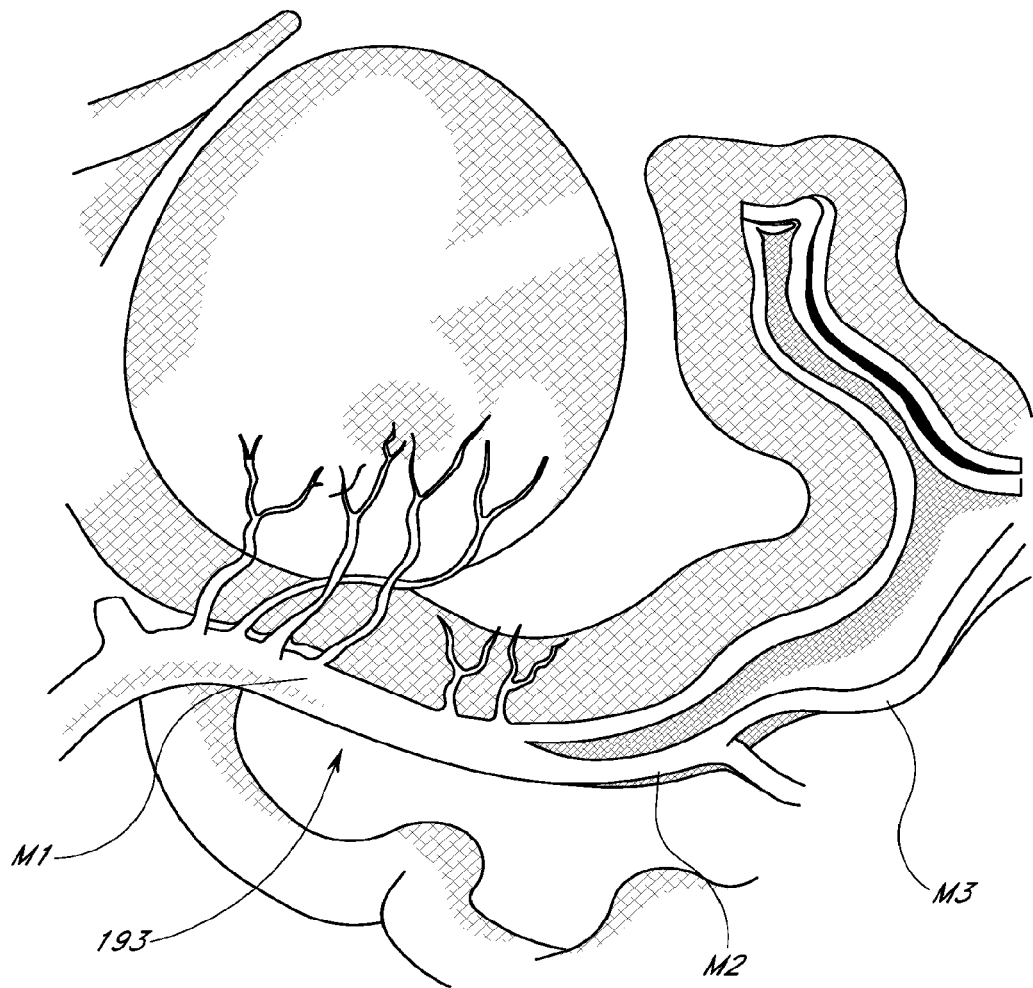
FIG. 15B is a detailed view of the middle cerebral artery and adjacent structures.

Referring to FIG. 15B, the left middle cerebral artery 193 comprises, in proximal to distal sequence, the M1 (horizontal) segment, the M2 (sylvian) segment, and the M3 (cortical) segments. At about the distal end of the M1 segment or the beginning of the M2 segment, the left middle cerebral artery 193 variably bifurcates or trifurcates into upper and lower divisions of the M2 segment.

Figure 15C:
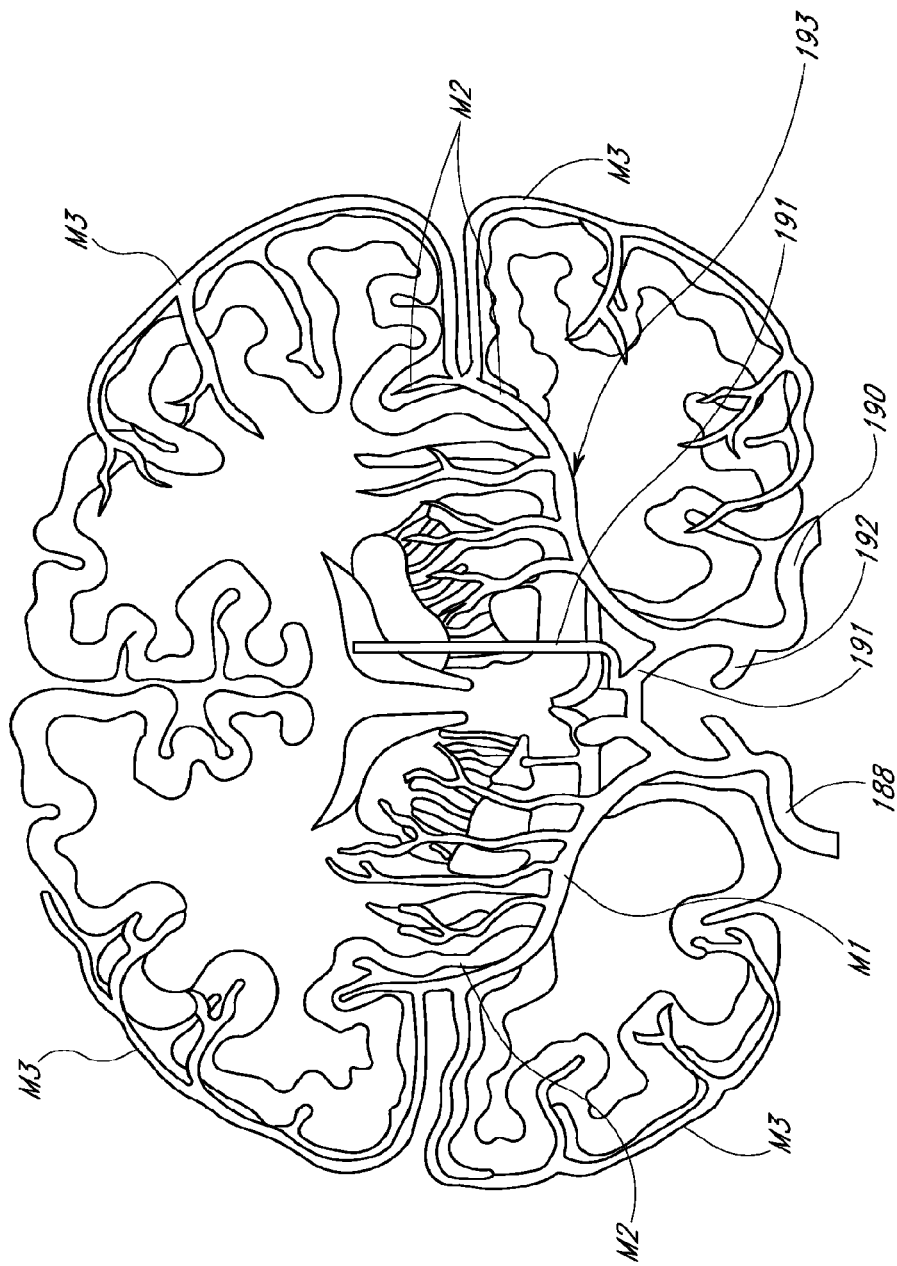
FIG. 15C is a schematic coronal sectional view of the brain and vasculature, including the middle cerebral artery and adjacent structures.

FIG. 15C is a schematic view of a coronal section through the brain, illustrating the left internal carotid artery 190 and right internal carotid artery 188. Also shown is the left posterior communicating artery 192, which branches off from the left internal carotid artery 190. The left internal carotid artery's 190 two terminal branches are also shown: the left anterior cerebral artery 191 and the left middle cerebral artery 193. The segments of the middle cerebral artery 193 are illustrated, including the M1, M2, and M3 segments.

Figure 15D:
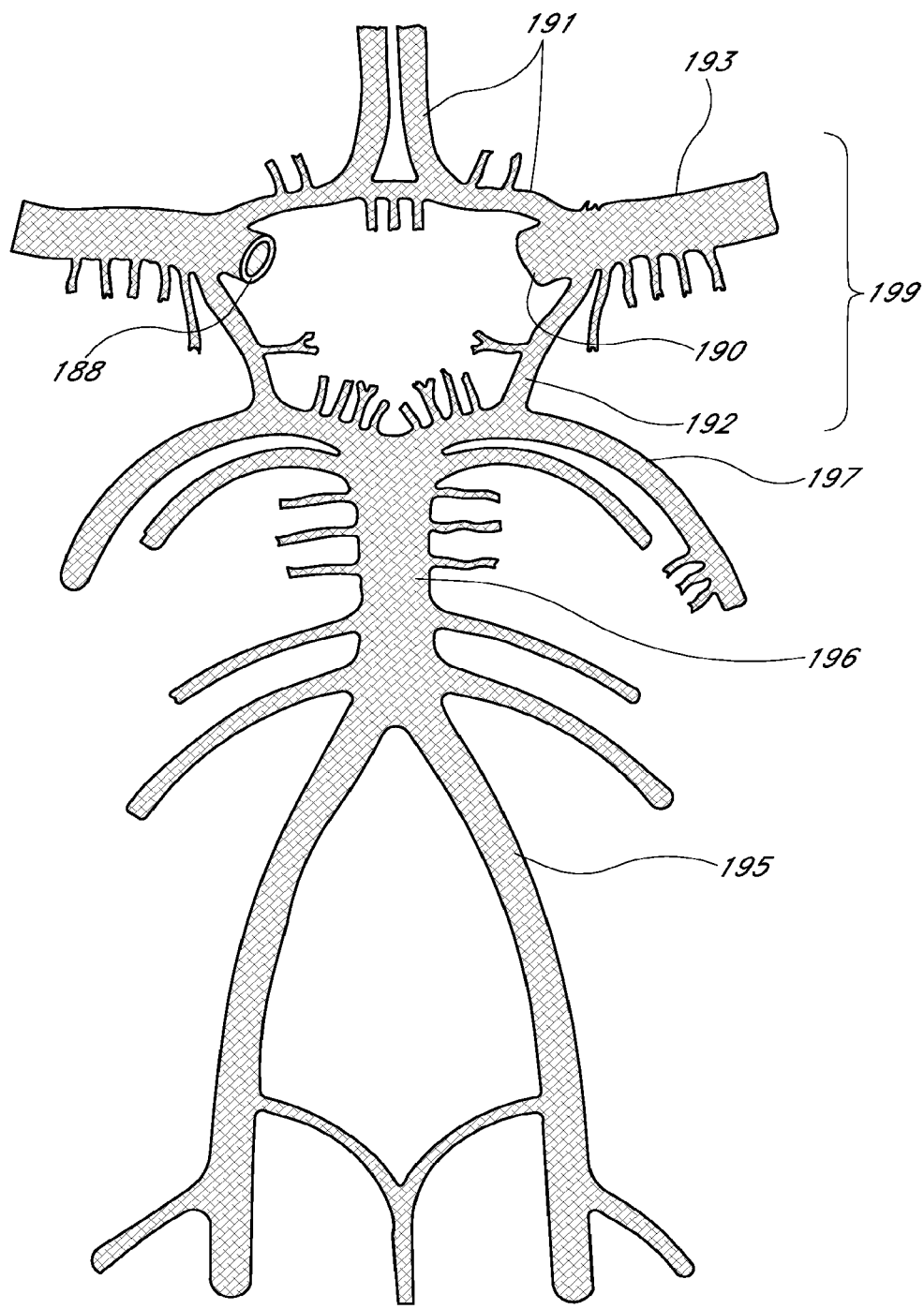
FIG. 15D is a schematic close-up view of the Circle of Willis and the anterior and posterior cerebral circulations.

FIG. 15D is a schematic close-up view of the Circle of Willis 199, which is the circular anastomosis of the anterior and posterior cerebral circulations. With regard to the anterior cerebral circulation, again shown are the right and left internal carotid arteries 188, 190, as well as the relationships (with reference again to the left side only) between the left internal carotid artery 190, the anterior communicating artery 203, the left posterior communicating artery 192, the left anterior cerebral artery 191, and the left middle cerebral artery 193. Also shown is the posterior cerebral circulation, including the right vertebral artery and left vertebral artery 195, the basilar artery 196, and its terminal branches, the right and left posterior cerebral arteries 197.

The internal carotid artery 190 makes several tight turns, including a 180-degree turn at its genu, which pose a challenge to any neurovascular catheter intended to reach the middle cerebral artery 193. The radius of curvature for this turn is approximately 5 mm, and the diameter of the internal carotid artery 190 is typically 3-4 mm. The most medial section of the petrosal portion of the internal carotid artery 190, just inferior to its entry into the cranial cavity, is known as the "carotid siphon."

According to cadaveric studies, the M1 segment of the middle cerebral artery 193 typically has a luminal diameter ranging between 2.5 and 5 mm, with a mean diameter of about 3 mm. The M2 segment of the middle cerebral artery 193 has a luminal diameter typically ranging between 1 and 3 mm, with a mean diameter of about 2 mm.

The neurothrombectomy catheter 200 in accordance with the present invention is adapted to navigate the arterial vasculature into at least the M3 segment of either the right or left middle cerebral artery 193, to remove both primary thrombi, which have formed in situ, and embolic material that has intially formed in the carotid arteries or in the heart and that has become lodged within the middle cerebral artery 193, frequently at a bifurcation. In addition, the neurothrombectomy catheter 200 in accordance with the present invention can remove both primary thrombi and emboli from other arteries, including the right and left internal carotid arteries 188, 190, the anterior communicating artery 203, the right and left posterior communicating artery 192, and the right and left anterior cerebral artery 191.

The neurothrombectomy catheter 200 is also adapted to traverse the right or left vertebral artery 195 (FIG. 15A) to reach thrombus formed or lodged in arteries of the posterior cerebral circulation, including the basilar artery 196 and its terminal branches, the right and left posterior cerebral artery 197, as well as the right and left posterior communicating artery 192.

FIGS. 16-22 illustrate one embodiment of the present invention, particularly adapted for use in remote tortuous anatomy, such as in the intracranial vasculature above the carotid arteries. Referring to FIGS. 16-22, the neurothrombectomy catheter 200 comprises an elongate flexible tubular body 202 having a proximal end 204 and a distal end 206. Proximal end 204 is adapted for coupling to a drive device such as those described elsewhere herein, for providing rotational energy as well as applying vacuum. For an intracranial application via femoral artery access, the tubular body 202 has an axial length within the range of from about 125 cm to about 200 cm and, in one embodiment, about 165 cm. The tubular body 202 is further provided with a cutting tip 208, coupled by drive shaft 210 to a source of rotational force at the proximal end 204 of the device 200, as has been discussed elsewhere herein.

The neurothrombectomy catheter 200 may be configured either as an over-the-wire or monorail device. In the monorail embodiment illustrated in FIG. 16, a guide wire lumen 212 extends from a distal guidewire port 214 to a proximal guidewire port 216. Proximal guidewire port 216 is spaced distally apart from the proximal end 204 of the tubular body 202 as is understood in the art. The proximal guidewire port 216 may be spaced proximally from the distal guidewire port 214 by a distance within the range of from about 10 cm to about 155 cm, depending upon the desired performance. In the illustrated embodiment, the proximal guidewire port 216 is spaced apart from the distal guidewire port 214 by a distance in excess of about 100 cm, such as about 145 cm. A marker band 220 having an axial length of about 5 mm is positioned approximately 1 cm proximally of guidewire port 216.

Figure 18:
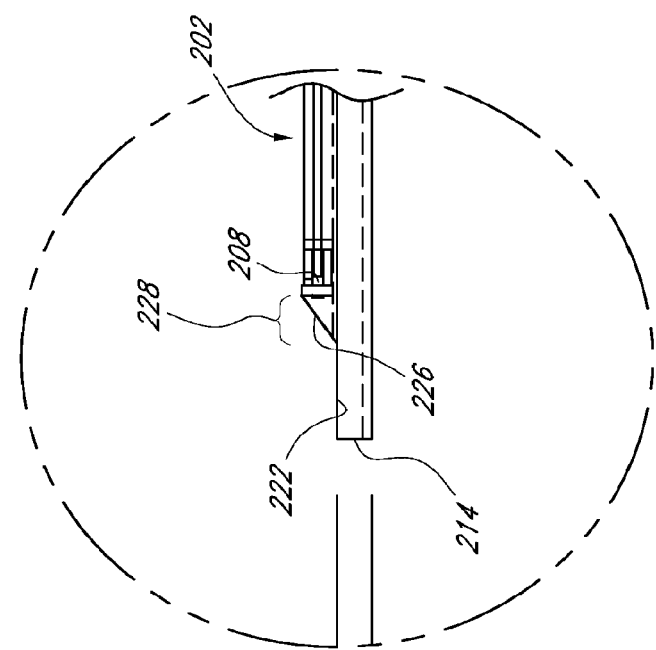
FIG. 18 is an enlarged detail view of the distal tip of the catheter of FIG. 16.

Referring to the detail view of FIG. 18, the distal guidewire port 214 is positioned on a distal advance segment 222 for enhancing the trackability of the neurothrombectomy catheter 200. The distal advance segment 222 has an outside diameter of preferably less than about 1 mm and, in one embodiment, about 0.58 mm. The axial length of the advance segment 222 is within the range of from about 1 mm to about 6 mm, and, in one embodiment, is about 4 mm.

Figure 19:
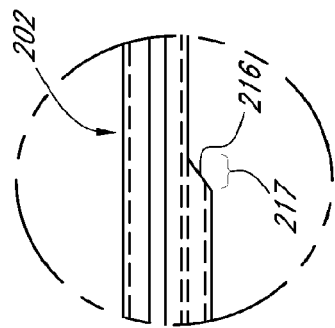
FIG. 19 is an enlarged detail view of the proximal opening to the guidewire lumen of the embodiment in FIG. 16.

Referring to the detail view shown in FIG. 19, the proximal guidewire access port 216 is provided with an angled opening having an axial length 217 within the range of from zero to about 8.0 mm and, in one embodiment, about 6.0 mm.

The cutting tip 208 is recessed within the tubular body 202, and exposed externally by way of a distal opening 226. Preferably, opening 226 is formed by an angled termination of the tubular body 202, over an axial length 228 of between about 0.5 mm and 3 mm and, in one embodiment, about 1.5 mm. The resulting angled transition between the advance segment 222 having guidewire lumen 212 therein, and the tubular body 202 having a cutting tip 208 therein enhances the crossability and tracking of the neurothrombectomy catheter 200 as will be appreciated by those of skill in the art in view of the disclosure herein.

In one embodiment, having the configuration illustrated in FIGS. 16 and 17A, the tubular body 202 has an outside diameter of about 0.047" and the aspiration lumen 218 has an inside diameter of about 0.037". The wall surrounding guidewire lumen 212 has an outside diameter of about 0.027" and an inside diameter of about 0.017". The greatest cross-sectional dimension, extending through both the aspiration lumen 218 and guidewire lumen 212, is about 0.069".

In general, the aspiration lumen 218 is provided with an inside diameter within the range of from about 0.015" to about 0.050", depending upon the intended application of the catheter and diameter of the drive shaft 210, to maintain a small O.D. but also optimize proximal flow of extracted material. Preferably, the aspiration lumen 218 is additionally configured to enable drug delivery, such as thrombolytics or other drugs as may be desired. This may be accomplished by providing a valve and side port on the proximal control, enabling access to the aspiration lumen 218, so that the vacuum source may be turned off and drug or other media may be infused through the aspiration lumen 218.

Any of a variety of additional features may be included to enhance performance. For example, in one embodiment, the inside diameter of the aspiration lumen 218 increases from the distal end 206 to the proximal end 204, to enhance proximal flowability of material and reduce the likelihood of occlusion. In addition, multiple sections of differing hardness or flexibility may be included, with hardness increasing from distal end 206 to proximal end 204, or flexibility increasing from proximal end 204 to distal end 206 to optimize pushability and flexibility.

In general, only about the distal most 15 cm to 30 cm of the tubular body 202 will extend beyond the distal end of the guide tube. Thus, at least the distal most 15 cm to 30 cm of the catheter 200 should exhibit a sufficiently low crossing profile, pushability and flexibility to navigate the middle cerebral artery. The proximal component of the catheter 200 may be provided with additional wall thickness, less flexible materials or greater diameter to enhance pushability without compromising the ability of the thrombectomy catheter 200 to reach remote intracranial treatment sites.

Either the proximal portion or distal portion or both of the neurothrombectomy device 200 may be provided with a wire braid or coil or polymer fiber reinforcement, to provide pushability and shape retention so that the tubular body 202 resists collapse under vacuum and resists kinking on tight radius turns. The tubular body 202 may be constructed such as by extrusion or coextrusion with wire or other reinforcement using materials such as polyethylene, PEBAX, polyethylene copolymers, polyurethanes, or other materials well known in the art.

The guidewire lumen 212 generally has an inside diameter within the range of from about 0.008" to about 0.024". Preferably, the guidewire lumen 212 will slideably accept a guidewire having a diameter within the range of from about 0.010" to about 0.014". The tubular wall which defines guidewire lumen 212 may be attached to the wall defining aspiration lumen 218 along the entire length of the guidewire lumen 212, or intermittently along the length of guidewire lumen 212. Thus, the two tubular walls may either be formed as a unitary extrusion, or may be separately produced and subsequently attached in a manufacturing step. The guidewire lumen 212 may extend in parallel to the aspiration lumen 218, or may be configured in a gradual spiral around the aspiration lumen 218. Preferably, the overall outside diameter of the thrombectomy catheter 200 is compatible for use with a seven French or smaller guide catheter.

Figure 20:
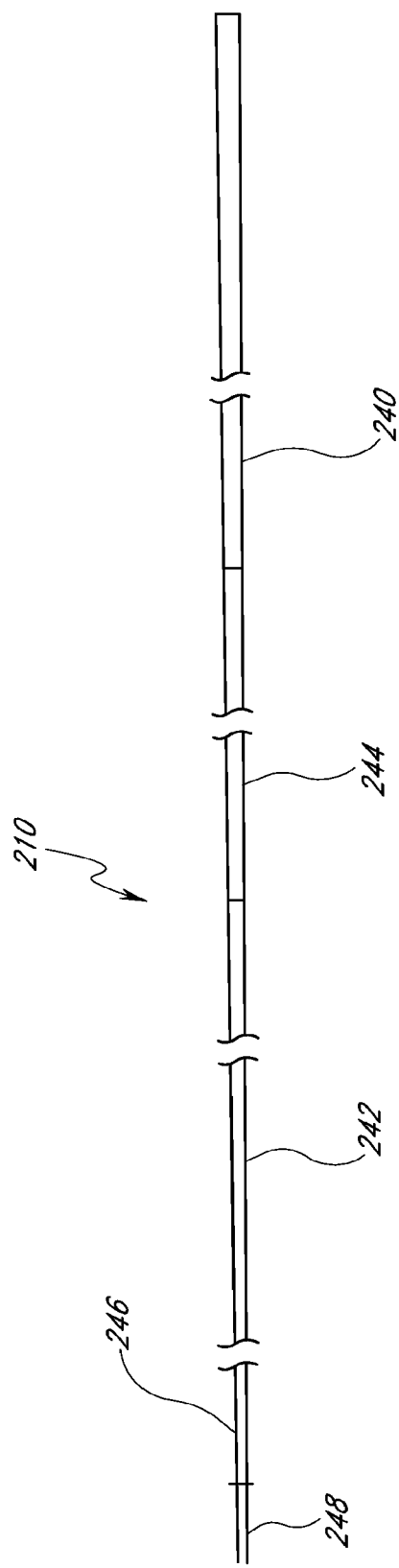
FIG. 20 is a side elevational view of a drive shaft which may be used in the embodiments of FIGS. 16 and 17A.

Referring to FIG. 20, there is illustrated one embodiment of a drive shaft 210 adapted for use in a monorail embodiment. In general, the drive shaft 210 has an axial length sufficient to extend from the proximal source of rotational energy to the cutting tip 208. In most embodiments, this will be within the range of from about 125 cm to about 200 cm. In one embodiment, the drive shaft 210 has an axial length of about 74". The outside diameter of the drive shaft may be anywhere within the range of from about 0.003" to about 0.020". Preferably, the drive shaft 210 is stepped or tapered from a relatively larger diameter at the proximal end to a relatively smaller diameter at the distal end to optimize torque transmission and flexibility.

Drive shaft 210 may be constructed either as a solid core wire, coil, or tube, depending upon the desired diameter and performance characteristics. Metals such as nitinol or stainless steel may be used, or Vectran or other polymer wound on a metal core.

In the illustrated embodiment of FIG. 20, the drive shaft 210 has a proximal, first section 240 having an axial length on the order of about 60" and an outside diameter of about 0.016"□0.004". A third section 242 is separated from the first section 240 by a second, tapered section 244. Tapered section 244 has an axial length of about 5 inches. The third section 242 has an axial length of about 8", and an outside diameter of about 0.007"□0.001". A distal portion 246 of the third section 242 may be provided with a gradual taper from the outside diameter of the proximal portion of third section 242 to the outside diameter of a fourth section 248. Fourth section 248 has an outside diameter of about 0.006"□0.001". The length of the tapered section 246 between the proximal portion of third section 242 and fourth section 248 is, in one embodiment, about 2". Any of a variety of alternate stepped configurations may be used, such as with two or three or four or five or more sections, as will be understood by those of skill in the art.

In an alternate embodiment, illustrated in cross-section at FIG. 17B, the neurothrombectomy catheter 200 is configured as an over-the-wire design. In this embodiment, in general, the drive shaft 210 is formed as a tubular element having the guidewire lumen 212 extending axially therethrough. The driveshaft 210 is thus configured in the form of a torque transmission tube 211, although the term "driveshaft" as used herein is generic to both the solid core or hollow versions unless further modified. The torque tube 211 is preferably provided with a thin wall, having as much flexibility as possible, while also retaining a high torque transmission capability and high resistance to collapse during navigation of tight radius turns and also under vacuum. The distal-most 10 to 30 cm of the torque tube 211 should be able to navigate a number of 1.0 cm or 0.5 cm or tighter radius sometimes non-coplanar turns of a vessel having a diameter of no greater than about 3 mm, such as the carotid siphon and middle cerebral arteries. Kink resistance is important in this embodiment, since the guidewire extending through the guidewire lumen 212 could bind if the inside diameter of the torque tube 211 is allowed to bend out of round while navigating or positioned within turns.

In general, the hollow torque tube 211 has an inside diameter within the range of from about 0.010' to 0.020", and minimized in an intracranial application. Preferably, the wall is constructed from two to five or more layers of material configured to optimize the physical properties discussed above. In one embodiment, four layers are included to permit bi-directional torque transmission. This enables reverse winding of the cutter tip as desired to dislodge blockages as has been discussed elsewhere herein.

The torque tube 211 may be formed by selecting a wire mandrel having a diameter corresponding to the desired inside diameter of the finished tube. The wire mandrel is provided with a polymer coating, of a heat softenable material such as polyethylene. A coil of metal ribbon (e.g., 0.001" by 0.004") is wound onto the polymer coating. The assembly is heated to allow the metal coil to be embedded or buried in the polymer. In one embodiment, the metal coil has a moderate pitch, such as on the order of 22°, to provide a balance between flexibility and crush resistance.

In a hollow drive shaft having bi-directional torque transmission capability, a first fiber layer is wound onto the polymer coating on top of the metal coil in a first wind direction at a very high pitch. Any of a variety of high tensile strength fibers, monofilament or braided, may be utilized, depending upon the desired wall thickness of the drive shaft and torque transmission capabilities. In one embodiment, Vectran fiber (obtained from Celanese) is used. One purpose of the high pitch first layer of fiber is to prevent axial elongation of the tube when rotated in either direction. This layer may be unnecessary in a unidirectional embodiment, and may be unnecessary in an embodiment which includes a floating drive shaft.

Two additional layers of polymer fiber are added in opposing wind directions, and embedded into the polymer coating on the metal coil. The exterior of the assembly is then smoothed off under heat, to maintain tight control of both the outside diameter and inside diameter. The mandrel may then be removed.

The foregoing torque tubes may be useful in any of the coronary, peripheral, neurological or other applications in which a rotational component is desired. The use of high tensile strength polymer fiber to provide torque strength instead of relying upon metal coils to provide torque strength exhibits improved flexibility and/or profile over prior designs in which the metal coil is utilized to provide torque strength. The hollow torque tube is particularly useful in an over the wire embodiment, in which the central lumen functions as the guidewire lumen.

In one multilayer embodiment, the wire of the inner metal wire coil has a maximum cross-section within the range of from about 0.0005" to about 0.004". The liquid crystal polymer fiber (e.g., Vectran) has a diameter within the range of from 0.00025" to about 0.002". The metal and/or polymer fiber windings may be encapsulated within any of a variety of suitable materials, including urethane and polyethylene, to produce an overall wall thickness within the range of from about 0.003" to about 0.008".

Alternatively, the torque tube 211 may be formed by spiral wrapping one or more wires or filaments without the use of a continuous polymer layer isolating the guidewire lumen 212 from the extraction lumen 218. For example, a tightly wound spring coil may be made from 0.006" diameter round wire, to have an inside diameter of about 0.014" and an O.D. of about 0.026". Other diameters or wire ribbon dimensions can be used depending upon the desired performance and size of the torque tube 211.

Figure 22:
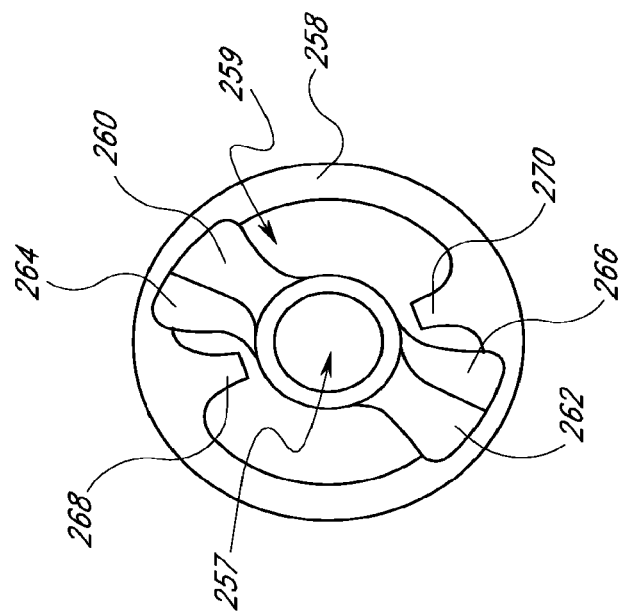
FIG. 22 is a distal end view of the cutting element of FIG. 21.
Figure 21:
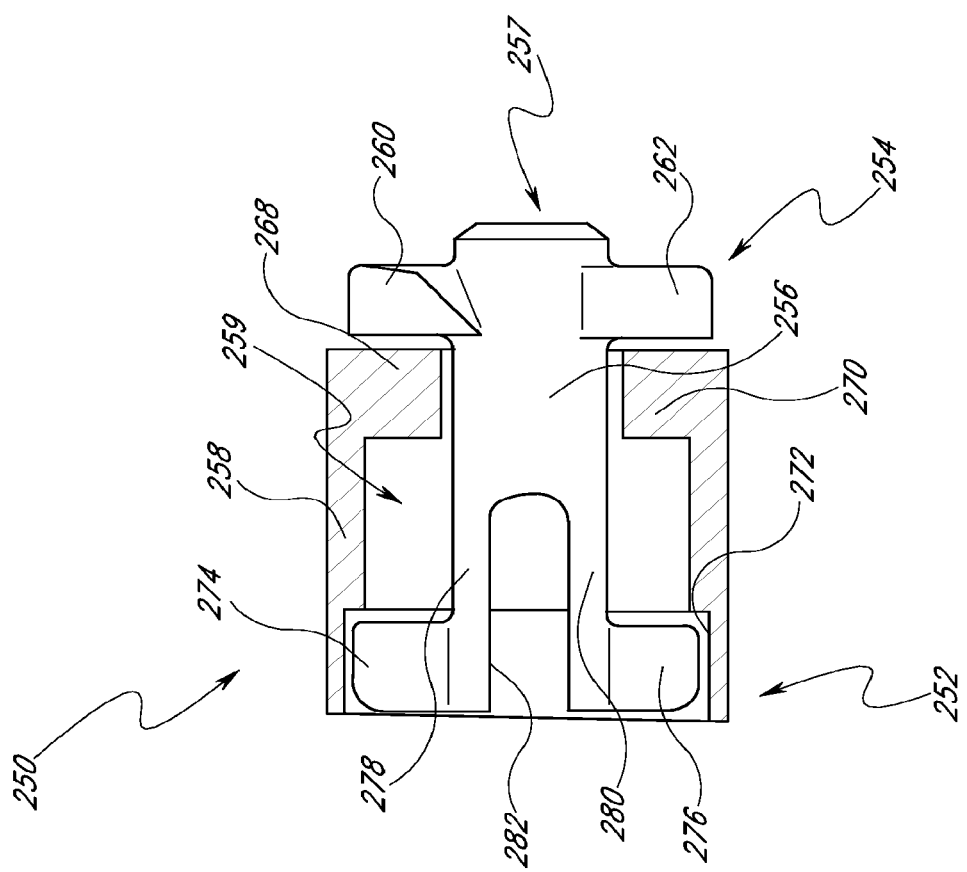
FIG. 21 is a partially sectioned side view of a cutting element used in the embodiment of FIG. 16.

Referring to FIGS. 21 and 22, there is illustrated a modified cutter tip 250, which is particularly adapted for the intracranial thrombectomy embodiment of the present invention. The cutter tip 250 comprises a proximal end 252 and a distal end 254. A tubular body 256 may be provided with a central aperture 257 for slidably receiving a guidewire therethrough, in the over-the-wire embodiment. The tubular body 256 is rotationally carried by a housing 258 in a manner similar to that described in connection with previous embodiments.

Note that the tubular body 256 can attach to the torque tube 211 (or other driveshaft 210), as illustrated in cross-section at FIG. 17B, by either having the tubular body 256 fit into the end of, or onto (i.e., partially around), the torque tube 211. Alternatively, in some embodiments the tubular body 256 can attach to the torque tube 211 by a laser weld or other weld, in a butt-joint configuration. In the over-the-wire embodiment, the tubular body 256 and the torque tube 211 are both hollow, to accommodate a central guidewire, which is 0.010" in a preferred embodiment.

In addition, a heat-shrinkable polymer tube can optionally be applied over any of the length of the tubular body 256, to improve pushability and limit vacuum loss.

At least a first and preferably first and second radially outwardly extending rotating cutting flanges 260, 262 are carried by the tubular body 256. In the illustrated embodiment, cutting flanges 260 and 262 are carried distally of the tubular body 256. However, the cutting flanges 260 and 262 may alternatively be carried within the tubular body 256. The cutting flanges 260 and 262 are preferably each provided with a cutting edge 264 and 266, to facilitate cutting material to be retrieved from the vessel. Once cut, thrombus material is pulled into an aspiration lumen 259 under negative (vacuum) pressure, and the material is subsequently moved proximally through the aspiration lumen 259 toward the proximal end 252 of the cutter tip 250 and toward the proximal end of the neurothrombectomy catheter 200.

Cutting edges 264 and 266 cooperate with first and second radially inwardly extending stationary cutting members 268 and 270. Stationary cutting members 268 and 270 are preferably integrally formed with the housing 258, or attached thereto in a subsequent manufacturing step. One or two or three or four or more stationary cutting members 268, 270 may be provided, depending upon the desired cutting characteristics of the cutter tip 250.

One or more of the stationary cutting members 268, 270 can act as a "wiper," to wipe or remove thrombotic material from the tubular body 256 and thus prevent the accumulation of debris that could partially or totally block the aspiration lumen 259. The stationary cutting members 268, 270 also act to complete the shearing mechanism that is begun by the cutting edge 264 and 266 of the cutting flanges 260 and 262. The stationary cutting members 268, 270 may also act to increase the mass of the distal end 254 of the cutter 250, in order to increase radiopacity.

The tubular body 256 is rotationally carried within the housing 258. First and second radially outwardly extending flanges 274, 276 are slidably received within an annular retaining race 272 in a manner similar to that previously described. The flanges 274 and 276 may be carried by deflectable arms 278 and 280, as has been discussed, for example, in connection with FIG. 3. This enables radially inward deflection of the flanges 274, 276, if desired, during the manufacturing process.

The proximal end 252 of the cutter tip 250 is provided with an attachment surface 282 such as a blind bore or throughbore for receiving the distal end of the torque wire or torque tube.

The overall length of the cutter tip 250 is generally no more than about 1.5 mm, and, in one embodiment, about 1.0 mm. The outside diameter of housing 258 is preferably no more than about 1.3 mm and, in one embodiment, is about 1.0. This embodiment is adapted to be positioned within the aspiration lumen 218, at the distal end 206 of the neuro thrombectomy catheter 200. In one embodiment, the housing 258 comprises stainless steel.

The cutter tip 250 may be secured to the drive shaft in any of a variety of ways as will be apparent to those of skill in the art in view of the disclosure herein. In accordance with one manufacturing technique, the cutter is bonded to the drive shaft by inserting the distal end of the drive shaft into the lumen defined by attachment surface 282 and bonding using a two-part epoxy such as EP42HT available from Master Bond. The adhesive is cured for approximately 2 hours at 135° C. The parts are preferably ultrasonically cleaned and rinsed in alcohol prior to bonding. The housing 258 is thereafter bonded to the interior of the aspiration lumen 218 using the same epoxy, and curing the adhesive for 12 hours or more at approximately 50° C. The housing 2580D and tubing ID are preferably mechanically roughened prior to bonding. In addition, the housing may be ultrasonically cleaned, for example, for 5 minutes, prior to bonding. Alternatively, the cutter tip 250 may be secured to the drive shaft by a laser weld.

Although this invention has been described in terms of certain preferred embodiments, other embodiments apparent to those of ordinary skill in the art are also within the scope of this invention. In addition, structures and features disclosed herein in connection with any one embodiment are intended to be incorporated, as desired, into any other embodiment. Accordingly, the scope of this invention is intended to be defined only by the claims that follow.

What is claimed is:

1. An intravascular medical device comprising:
   an elongate tubular body having a proximal end, a distal end, and an outer diameter;
   a housing coupled to the distal end of the elongate tubular body, the housing having distal and proximal sections, each section having distal and proximal ends, the proximal end of the proximal section connected to the tubular body, the proximal end of the distal section connected to the distal end of the proximal section, an inner surface of the distal section of the housing defining an interior space, the distal section of the housing including a distal segment shaped to extend radially inwardly with respect to a longitudinal axis of the housing to define an opening at the distal end of the distal section of the housing;
   a rotatable cutting element positioned within the interior space of the housing, the rotatable cutting element having distal and proximal ends and a lumen extending between the proximal and distal ends, the cutting element having a first outer dimension smaller than an inner dimension of the housing and larger than a dimension of the opening at the distal end of the distal section of the housing and larger than a dimension of an opening in the distal end of the proximal section of the housing;
   a flexible drive shaft connected to the rotatable cutting element extending through the elongate tubular body, the flexible drive shaft having a lumen aligned with the lumen of the cutting element, the lumens being sized and configured to accept a guidewire; and
   a control at the proximal end of the elongate tubular body and comprising a drive motor configured to transmit rotation to the flexible drive shaft,
   wherein the cutting element has a second outer dimension smaller than the dimension of the opening at the distal end of the distal section of the housing,
   wherein the cutting element comprises an outer surface with at least one cutting blade extending outwardly from the outer surface, the cutting blade extending in a helical pattern for one revolution or less about the cutting element,
   wherein a distal portion of the cutting blade extends through the opening at the distal end of the distal section of the housing.

2. The intravascular medical device of claim 1 wherein the cutting blade is a plurality of cutting blades.

3. The intravascular medical device of claim 1 wherein the at least one cutting blade extends in a helical pattern for about one-half to one revolution about the cutting element.

4. The intravascular medical device of claim 1 wherein the proximal end of the distal section of the housing is connected to the distal end of the proximal section of the housing by laser welding.

5. The intravascular medical device of claim 1 wherein the distal and proximal sections of the housing are sized and configured to capture the cutting element within the interior space of the housing.

6. The intravascular medical device of claim 1 wherein the distal segment comprises an inwardly extending flange.

7. The intravascular medical device of claim 1 wherein the proximal section of the housing and the tubular body have concentric overlapping portions.

8. The intravascular medical device of claim 1 wherein the proximal section of the housing comprises a bearing surface for bearing against a surface of the cutting element.

9. The intravascular medical device of claim 1 wherein the cutting blade has a constant pitch.

10. The intravascular medical device of claim 1 wherein the cutting blade has a cross-section that varies along an axial length of the cutting blade.

11. The intravascular medical device of claim 10 wherein the cross-section of the cutting blade at a distal end of the cutting blade is less than a cross-section of the cutting blade at a proximal end of the cutting blade.

12. An intravascular medical device comprising:
    an elongate tubular body having a proximal end, a distal end, and an outer diameter; a housing coupled to the distal end of the elongate tubular body, the housing having a proximal end and a distal end and an opening at the distal end;
    a rotatable cutting element including a cylindrical body and at least one cutting blade, the cylindrical body having distal and proximal ends and a lumen extending between the distal and proximal ends, the cylindrical body further having an outer surface having a substantially constant diameter between the distal and proximal ends, the at least one cutting blade extending outwardly from the outer surface in a helical pattern for about one-half to one revolution about the cylindrical body of the cutting element, the rotatable cutting element being configured to axially displace relative to a longitudinal axis of the housing along a limited range of motion between a first position, in which the cylindrical body is recessed within the housing, and a second position, in which the cylindrical body at least partially protrudes through the opening in the distal end of the housing, wherein at least a portion of the cutting blade is exposed beyond the housing in the second position;
    a flexible drive shaft connected to the rotatable cutting element extending through the elongate tubular body, the drive shaft having a lumen aligned with the lumen of the cylindrical body of the cutting element, the lumens being sized and configured to accept a guidewire; and
    a control at the proximal end of the elongate tubular body and comprising a drive motor configured to transmit rotation to the flexible drive shaft.

13. The intravascular medical device of claim 12 wherein the cutting blade is a plurality of cutting blades.

14. The intravascular medical device of claim 12 wherein the housing comprises distal and proximal sections, the proximal section having a proximal end connected to the tubular body, the distal section having a proximal end connected to a distal end of the proximal section, the cylindrical body being recessed within the distal section when the cutting element is in the second position.

15. The intravascular medical device of claim 14 wherein the proximal end of the distal section of the housing is connected to the distal end of the proximal section of the housing by laser welding.

16. The intravascular medical device of claim 14 wherein the proximal section of the housing and the tubular body have concentric overlapping portions.

17. The intravascular medical device of claim 12 wherein the cutting blade has a constant pitch.

18. The intravascular medical device of claim 12 wherein the cutting blade has a cross-section that varies along an axial length of the cutting blade.

19. The intravascular medical device of claim 18 wherein the cross-section of the cutting blade at a distal end of the cutting blade is less than a cross-section of the cutting blade at a proximal end of the cutting blade.

* * * * *